(12) United States Patent
Kischnick et al.

(10) Patent No.: US 12,295,365 B2
(45) Date of Patent: May 13, 2025

(54) COMPOSITION INCLUDING AN ANTIMICROBIAL BOOSTING AGENT INCLUDING A SULTAINE AND METHODS OF INCREASING THE ANTIMICROBIAL EFFECTIVENESS OF A COMPOSITION

(71) Applicant: KIMBERLY-CLARK WORLDWIDE, INC., Neenah, WI (US)

(72) Inventors: Andrew R. Kischnick, Appleton, WI (US); Corey T. Cunningham, Larsen, WI (US); Scott W. Wenzel, Neenah, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 17/264,326

(22) PCT Filed: Jul. 31, 2018

(86) PCT No.: PCT/US2018/044555
§ 371 (c)(1),
(2) Date: Jan. 29, 2021

(87) PCT Pub. No.: WO2020/027798
PCT Pub. Date: Feb. 6, 2020

(65) Prior Publication Data
US 2021/0298302 A1    Sep. 30, 2021

(51) Int. Cl.
*A01N 41/04* (2006.01)
*A01N 25/02* (2006.01)
*A01N 25/34* (2006.01)

(52) U.S. Cl.
CPC ............ *A01N 41/04* (2013.01); *A01N 25/02* (2013.01); *A01N 25/34* (2013.01)

(58) Field of Classification Search
CPC ........ A01N 41/04; A01N 25/34; A01N 25/02; A61K 8/466; A61K 31/05; A61K 31/16; A61K 31/185; A61K 31/205; A61K 45/06; A61K 8/0208; A61K 2300/00; A61P 31/04; A61Q 17/005
See application file for complete search history.

(56) References Cited

U.S. PATENT DOCUMENTS

| | | | |
|---|---|---|---|
| 4,183,952 A | 1/1980 | Michaels | |
| 4,769,169 A | 9/1988 | Fishlock-Lomax | |
| 6,121,219 A | 9/2000 | Herdt et al. | |
| 6,579,514 B1 | 6/2003 | Hall et al. | |
| 6,669,931 B2 * | 12/2003 | Lynch | A61K 6/78 424/52 |
| 6,861,397 B2 | 3/2005 | Seitz, Jr. et al. | |
| 7,094,742 B2 | 8/2006 | Gaudreault | |
| 8,241,613 B2 | 8/2012 | Candau et al. | |
| 8,470,755 B1 | 6/2013 | Tajmamet et al. | |
| 8,632,761 B2 * | 1/2014 | Doi | C08B 11/193 424/70.13 |
| 8,883,848 B2 | 11/2014 | Bolduc et al. | |
| 9,000,105 B2 | 4/2015 | Lombardi | |
| 9,451,763 B2 | 9/2016 | Daigle et al. | |
| 9,555,167 B2 | 1/2017 | Schmid et al. | |
| 2002/0002124 A1 | 1/2002 | Biedermann et al. | |
| 2002/0022660 A1* | 2/2002 | Jampani | A61P 31/04 514/635 |
| 2002/0061286 A1 | 5/2002 | Durden | |
| 2007/0036832 A1 | 2/2007 | Williams et al. | |
| 2010/0069861 A1 | 3/2010 | Yao et al. | |
| 2010/0261630 A1 | 10/2010 | Barnhart et al. | |
| 2011/0124772 A1 | 5/2011 | Wang et al. | |
| 2014/0142197 A1* | 5/2014 | Daigle | A01N 25/02 514/731 |
| 2015/0320913 A1 | 11/2015 | Song et al. | |
| 2015/0335555 A1 | 11/2015 | Dobrowolski et al. | |
| 2015/0373970 A1 | 12/2015 | Truong et al. | |
| 2016/0106093 A1 | 4/2016 | Hu et al. | |

(Continued)

FOREIGN PATENT DOCUMENTS

| | | |
|---|---|---|
| CN | 102846491 A | 1/2013 |
| CN | 102860778 A | 1/2013 |
| CN | 104450284 A | 3/2015 |

(Continued)

OTHER PUBLICATIONS

Co-pending U.S. Appl. No. 17/264,344, filed Jan. 29, 2021, by Kischnick et al. for "Composition Including an Antimicrobial Boosting Agent Including an Amphocarboxylate and Methods of Increasing the Antimicrobial Effectiveness of a Composition".
Huggies® Cleaning Wipes, Jul. 31, 2018, https://www.huggies.com/en-us/wipes/cleansing-wipes.
Huggies Natural Care® Plus, Jul. 31, 2018, https://www.huggies.com/en-us/wipes/natural-care-plus.
Huggies Natural Care® Wipes, Jul. 31, 2018, https://www.huggies.com/en-us/wipes/natural-care.
Huggies® One & Done@ Refreshing Wipes, Jul. 31, 2018, https://www.huggies.com/wipes/one-and-done-refreshing.

(Continued)

*Primary Examiner* — Mina Haghighatian
*Assistant Examiner* — Nathan W Schlientz
(74) *Attorney, Agent, or Firm* — KIMBERLY-CLARK WORLDWIDE, INC.

(57) ABSTRACT

Antimicrobial compositions can include an antimicrobial boosting agent that increases the antimicrobial effectiveness of the composition. A composition can include a carrier providing at least 90% of a total weight of the composition and an antimicrobial agent. The composition can also include an antimicrobial boosting agent comprising a sultaine. The antimicrobial boosting agent can provide 1.0% or less of the total weight of the composition. The composition can be substantially free from a short-chain alcohol.

8 Claims, 1 Drawing Sheet

(56) References Cited

U.S. PATENT DOCUMENTS

2016/0324971 A1    11/2016  Kilic et al.

FOREIGN PATENT DOCUMENTS

| CN | 104292961 | B |   | 5/2017 |
|----|-----------|---|---|--------|
| CN | 106619232 | A |   | 5/2017 |
| CN | 106929207 | A | * | 7/2017 |
| CN | 107595731 | A |   | 1/2018 |
| DE | 292828    | A5|   | 8/1991 |
| EP | 1857535   | B1|   | 12/2010 |
| KR | 101240511 | B1|   | 3/2013 |
| WO | 03031546  | A1|   | 4/2003 |
| WO | 08031104  | A2|   | 3/2008 |
| WO | 11101239  | A2|   | 8/2011 |
| WO | 14097005  | A1|   | 6/2014 |
| WO | 14121189  | A1|   | 8/2014 |
| WO | 17072482  | A1|   | 5/2017 |
| WO | 18143911  | A1|   | 8/2018 |

OTHER PUBLICATIONS

Huggies® Simply Clean® Fragrance Free, Jul. 31, 2018, https://www.huggies.com/en-us/wipes/simply-clean.

Huggies® Simply Clean® Fresh Wipes, Jul. 31, 2018, https://www.huggies.com/en-us/wipes/simply-clean-fresh.

Wieczorek, Daria, et al., "Surface and Antimicrobial Activity of Sulfobetaines", May 31, 2016, Journal of Surfactants and Detergents, https://link.springer.com/article/10.1007/s11743-016-1838-3.

Tiecco, Matteo, et al., "Ionic Conductivity as a Tool to Study Biocidal Activity of Sulfobetaine Micelles against *Saccharomyces cerevisiae* Model Cells", Jan. 11, 2016, Langmuir, http://pubs.acs.org/doi/abs/10.1021/acs.langmuir.5b04077?src=recsys&journalCode=langd5.

Birnie, Christine R., et al., "Antimicrobial Evaluation of N-Alkyl Betaines and N-Alkyl-N, N-Dimethylamine Oxides with Variations in Chain Length", Sep. 1, 2000, Antimicrobial agents and chemotherapy, http://aac.asm.org/content/44/9/2514.full.

Julich, W.-D., et al., "Synthesis and antimicrobial effect of selected n-alkylamino-4-sulphonyl-methyl-1, 1-dimethyl-pyrrolidinium betaines", Jan. 1, 1994, Hygiene + Medizin, https://www.researchgate.net/publication/298001273_Synthesis_and_antimicrobial_effect_of_selected_n-alkylamino-4-sulphonyl-methyl-11-dimethyl-pyrrolidinium_betaines.

Chen, Yuxiang, et al., "Enhanced Water-solubility, Antibacterial Activity and Biocompatibility upon Introducing Sulfobetaine and Quaternary Ammonium to Chitosan", Jun. 5, 2016, Carbohydrate Polymers, http://www.sciencedirect.com/science/article/pii/S0144861716300376?via%3Dihub.

Pu, Yuji, et al., "Synthesis and Antibacterial Study of Sulfobetaine/Quaternary Ammonium-Modified Star-Shaped Poly [2-(dimethylamino)ethyl methacrylate]-Based Copolymers with an Inorganic Core", Dec. 6, 2016, Biomacromolecules, http://pubs.acs.org/doi/abs/10.1021/acs.biomac.6b01279?journalCode=bomaf6.

He, Liang, et al., "Constructing safe and durable antibacterial textile surfaces using a robust graft-to strategy via covalent bond formation", Nov. 3, 2016, Scientific report, http://www.nature.com/articles/srep36327.

Chen, Shiguo, et al., "Synthesis and characterization of siloxane sulfobetaine antimicrobial agents", Mar. 23, 2011, Surface Science, http://www.sciencedirect.com/science/article/pii/S0039602811001002.

Mo, Funian, et al., "Novel zwitterionic polyurethanes with good biocompatibility and antibacterial activity", Apr. 15, 2015, Materials Letters, http://www.sciencedirect.com/science/article/pii/S0167577X15001056.

He, Liang et al., "Non-leaching and durable antibacterial textiles finished with reactive zwitterionic sulfobetaine", Feb. 25, 2017, Journal of Industrial and Engineering Chemistry, https://www.researchgate.net/publication/310381804_Non-leaching_and_durable_antibacterial_textiles_finished_with_reactive_zwitterionic_sulfobetaine.

El-Dougdoug, W.I.A et al., "Amphoteric surface active agents with heterocyclic ring based on industrial wastes", April and May 2012, Egyptian Journal of Chemistry, http://ejchem.journals.ekb.eg/article_1390.html.

Gottschick, Cornelia, et al., "Screening of Compounds against Gardnerella vaginalis Biofilms", Apr. 25, 2016, PLoS One, http://journals.plos.org/plosone/article?id=10.1371/journal.pone.0154086.

Patrone, Vania, et al., "In Vitro Synergistic Activities of Essential Oils and Surfactants in Combination with Cosmetic Preservatives Against Pseudomonas aeruginosa and *Staphylococcus aureus*", Nov. 1, 2009, Current microbiology, https://www.researchgate.net/publication/38097086_In_Vitro_Synergistic_Activities_of_Essential_Oils_and_Surfactants_in_Combination_with_Cosmetic_Preservatives_Against_Pseudomonas_aeruginosa_and_Staphylococcus_aureus.

Calis, S., et al., "A non-antibiotic antimicrobial mixture (C31G): evaluation of the antimicrobial efficiency of C31G on vaginal cultures", Oct. 1, 1992, Boll Chim Farm., https://www.ncbi.nlm.nih.gov/pubmed/1492969.

Gawish, S.M., et al., "Synthesis and properties of amphoteric surfactants", Jun. 6, 1980, Journal of the American Oil Chemists' Society, https://link.springer.com/article/10.1007/BF02899470.

* cited by examiner

ND METHODS
COMPOSITION INCLUDING AN ANTIMICROBIAL BOOSTING AGENT INCLUDING A SULTAINE AND METHODS OF INCREASING THE ANTIMICROBIAL EFFECTIVENESS OF A COMPOSITION

TECHNICAL FIELD

Disclosed are antimicrobial compositions and methods of inhibiting microbial growth. More specifically, disclosed is an antimicrobial composition that includes an antimicrobial agent and an antimicrobial boosting agent including a sultaine that provides enhanced antimicrobial effectiveness. The antimicrobial composition may be applied to or incorporated into articles such as wipes, or into solutions, ointments, lotions, creams, salves, aerosols, gels, suspensions, sprays, foams, washes, or the like.

BACKGROUND OF THE DISCLOSURE

Preservatives are an often utilized component in cosmetic, pharmaceutical, household, industrial, and personal care products to ensure that a product stays fresh on the shelf, doesn't experience spoilage, and remains free from bacterial growth. In particular, because personal care products may be used to directly contact skin or mucosa such as around body orifices where the potential for transfer of materials from the product to the consumer may be a concern, it is generally good practice to reduce contamination of the product in every possible way. The need to control microbiological growth is particularly acute in water based products such as non-ionic oil-in-water emulsions and in pre-impregnated wipes such as wet wipes.

Multiple options for antimicrobial agents that prevent microbial growth, such as formaldehyde donors or parabens, have existed throughout history and these antimicrobial agents were highly efficacious and allowed for relatively easy preservation of personal care products. Recently, traditional antimicrobial agents have been less desirable components in personal care products in view of new regulations and consumer perceptions, thus limiting the options for preventing microbial growth in certain products. Additionally, there has recently been a desire among an increasingly large segment of consumers for products with low concentrations of non-water ingredients, and thus, high concentrations of water. At the same time, these consumers still desire a high level of product performance that can only be delivered effectively through the use of specialized ingredients. Therefore, it would be highly advantageous to identify ingredients that can deliver a high level of product benefits at low concentrations or that can deliver multiple product benefits. Reducing concentrations of non-water ingredients also typically provides the added benefit of reducing raw material costs.

Alternative antimicrobial agents have been explored. For example, some organic acids and their derivatives have been used for their antimicrobial effect and other ingredients that provide an antimicrobial effect in addition to another purpose (referred to as "multifunctional ingredients") have been used. However, these alternative antimicrobial agents often have limitations. As a primary point, these alternative antimicrobial agents often have reduced efficacy, resulting in the necessity to use them in higher concentrations to maintain acceptable antimicrobial efficacy, resulting in higher cost as they usually tend to be more expensive than traditional preservatives. Organic acids and some multifunctional ingredients that possess an antimicrobial effect can also tend to have an inherent odor, thus limiting the concentration that can be used without negatively affecting the overall olfactory perception of the product. Another drawback to many organic acids is that they are often only efficacious in the acid form, thus limiting their use to compositions having a narrow and low pH range. Many of the multifunctional ingredients providing an antimicrobial effect, as well as organic acids, frequently exhibit limited water solubility characteristics. Furthermore, many multifunctional ingredients having an antimicrobial effect can have poor tactile attributes, limiting the amount that can be used and still provide a consumer-acceptable formulation. Because of these drawbacks, it becomes difficult to find an acceptable balance between the need for antimicrobial efficacy and consumer acceptability of an antimicrobial composition.

Thus, there remains a need for antimicrobial compositions that include an antimicrobial agent and an antimicrobial boosting agent that can be used in a composition to increase the antimicrobial effect of the composition to allow for the usage of milder antimicrobial agents and at lower concentrations to provide satisfactory antimicrobial efficacy and reduced cost, while still maintaining acceptable stability and product aesthetics.

SUMMARY OF THE DISCLOSURE

In one aspect of the disclosure, a composition can include a carrier providing at least 90% of a total weight of the composition. The composition can also include an antimicrobial agent. The composition can further include an antimicrobial boosting agent. The antimicrobial boosting agent can include a sultaine. The antimicrobial boosting agent can provide 1.0% or less of the total weight of the composition. The composition can be substantially free from a short-chain alcohol.

In another aspect, a method of increasing the effectiveness of an antimicrobial composition is provided. The method can include providing an antimicrobial composition. The antimicrobial composition can include a carrier. The antimicrobial composition can also include an antimicrobial agent. The composition can be substantially free from a short-chain alcohol. The method can also include selecting an antimicrobial boosting agent comprising a sultaine. The antimicrobial boosting agent can be selected to increase the antimicrobial effectiveness of the antimicrobial agent. The method can additionally include adding the antimicrobial boosting agent to the antimicrobial composition to increase the antimicrobial effectiveness of the antimicrobial composition.

In yet another aspect, a wet wipe is provided. The wet wipe can include a substrate and a wetting composition. The wetting composition can be applied to the substrate. The wetting composition can include a carrier. The carrier can provide at least 90% of a total weight of the wetting composition. The wetting composition can also include an antimicrobial agent. The wetting composition can additionally include an antimicrobial boosting agent. The antimicrobial boosting agent can include a sultaine. The antimicrobial boosting agent can provide 1.0% or less of the total weight of the wetting composition. The wetting composition can be substantially free from a short-chain alcohol.

DETAILED DESCRIPTION OF THE DISCLOSURE

Figure 1:
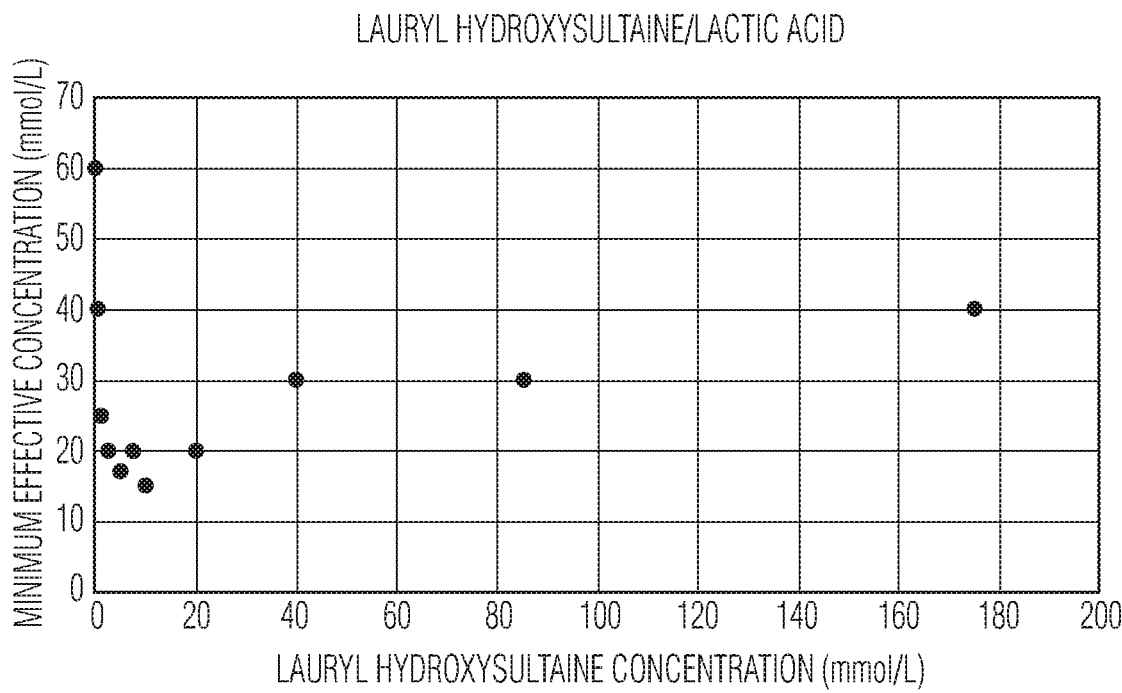
FIG. 1 is a graph displaying the results of Minimum Effective Concentration (MEC) testing for a composition including the antimicrobial agent of lactic acid and an antimicrobial agent of lauryl hydroxysultaine of varying concentrations of the antimicrobial boosting agent.

The present disclosure is directed to antimicrobial compositions and methods of inhibiting microbial growth in which the antimicrobial compositions include an antimicrobial agent and an antimicrobial boosting agent including a sultaine. In preferred embodiments, the antimicrobial compositions including an antimicrobial boosting agent can be substantially free of a short-chain alcohol. The antimicrobial compositions could be utilized in a variety of cosmetic, pharmaceutical, household, industrial, and personal care products. Suitable products could include, but are not limited to: shampoo, conditioner, soaps, moisturizers, skin protective, skin restorative and skin strengthening products, hand sanitizers, skin and body cleansers, deodorants, sunscreens, lip balms, lip sticks, disinfectants, hard surface cleansers, dish soaps, laundry detergents and the like. These products could take a variety of forms including but not limited to water-thin liquids, aqueous solutions, gels, balms, lotions, ointments, suspensions, creams, milks, salves, ointments, pastes, powders, aerosols, sprays, mists, mousses, emulsions, oils, foams, washes, solid sticks, aerosols, water, oil or silicone solutions or emulsions, including water in oil, oil in water, silicone in water, water in silicone and the like. Additionally, as will be described in further detail below, the forms of these products may be used in conjunction with a substrate, such that the solution may be added to the substrate for delivery. Suitable substrate based products include, but are not limited to: wipes, facial tissue, bath tissue, paper towels, napkins, diapers, diaper pants, feminine hygiene products (tampons, pads), gloves, socks, masks or combinations thereof.

Within each of the above envisioned products, the antimicrobial boosting agents could be used with a variety of ingredients utilized in cosmetic, pharmaceutical, household, industrial, and personal care products. Suitable ingredients, some of which will be described in further detail herein, can come from a broad category range including, but not limited to antimicrobial agents/preservatives, aqueous solvents, non-aqueous solvents, humectants, emollients, surfactants, emulsifiers, builders, sequestrants, chelators, preservatives, pH modifiers, disinfectants, colorants, rheology modifiers, antioxidants, anti-parasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, deodorants, antiperspirants, fragrance, and various other optional ingredients as are known by one skilled in the art.

The term "meltblown" refers herein to fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which can be a microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al., which is incorporated herein by reference. Meltblown fibers are microfibers which may be continuous or discontinuous, are generally smaller than about 0.6 denier, and may be tacky and self-bonding when deposited onto a collecting surface.

The term "nonwoven" refers herein to materials and webs of material which are formed without the aid of a textile weaving or knitting process. The materials and webs of materials can have a structure of individual fibers, filaments, or threads (collectively referred to as "fibers") which can be interlaid, but not in an identifiable manner as in a knitted fabric. Nonwoven materials or webs can be formed from many processes such as, but not limited to, meltblowing processes, spunbonding processes, carded web processes, etc.

Antimicrobial Agents

The antimicrobial compositions of this disclosure can include one or more antimicrobial agents. The antimicrobial agents used in the antimicrobial compositions can be "traditional antimicrobial agents," referring to compounds that have been historically recognized by regulatory bodies as providing an antimicrobial effect, such as those listed in the European Union's Annex V list of preservatives allowed in cosmetics products. Traditional antimicrobial agents include, but are not limited to: propionic acid and salts thereof; salicylic acid and salts thereof; sorbic acid and salts thereof; benzoic acid and salts and esters thereof; formaldehyde; paraformaldehyde; o-phenylphenol and salts thereof; zinc pyrithione; inorganic sulfites; hydrogen sulfites; chlorobutanol; benzoic parabens, such as methylparaben, propylparaben, butylparaben, ethylparaben, isopropylparaben, isobutylparaben, benzylparaben, sodium methylparaben and sodium propylparaben; dehydroacetic acid and salts thereof; formic acid and salts thereof; dibromohexamidine isethionate; thimerosal; phenylmercuric salts; undecylenic acid and salts thereof; hexetidine; 5-bromo-5-nitro-1,3-dioxane; 2-bromo-2-nitropropane-1,3,-diol; dichlorobenzyl alcohol; triclocarban; p-chloro-m-cresol; triclosan; chloroxylenol; imidazolidinyl urea; polyaminopropyl biguanide; phenoxyethanol, methenamine; quaternium-15; climbazole; DMDM hydantoin; benzyl alcohol; piroctone olamine; bromochlorophene; o-cymen-5-ol; methylchloroisothiazolinone; methylisothiazolinone; chlorophene; chloroacetamide; chlorhexidine; chlorhexidine diacetate; chlorhexidine digluconate; chlorhexidine dihydrochloride; phenoxyisopropanol; alkyl (C12-C22) trimethyl ammonium bromide and chlorides; dimethyl oxazolidine; diazolidinyl urea; hexamidine; hexamidine diisethionate; glutaral; 7-ethylbicyclooxazolidine; chlorphenesin; sodium hydroxymethylglycinate; silver chloride; benzethonium chloride; benzalkonium chloride; benzalkonium bromide; benzylhemiformal; iodopropynyl butylcarbamate; ethyl lauroyl arginate HCl; citric acid; and silver citrate.

Additionally or alternatively, non-traditional antimicrobial agents can be used an antimicrobial agent in the antimicrobial composition of the present disclosure. Non-traditional antimicrobial agents, as used herein, can be compounds that are known to exhibit antimicrobial effects in addition to their primary functions, but that have not historically been recognized as antimicrobial agents by regulatory bodies (such as on the European Union's Annex V list). Examples of these non-traditional antimicrobial agents include, but are not limited to, hydroxyacetophenone, caprylyl glycol, sodium coco-PG dimonium chloride phosphate, phenylpropanol, lactic acid and salts thereof, caprylhydroxamic acid, levulinic acid and salts thereof, sodium lauroyl lactylate, phenethyl alcohol, sorbitan caprylate, glyceryl caprate, glyceryl caprylate, ethylhexylglycerin, p-anisic acid and salts thereof, gluconolactone, decylene glycol, 1,2-hexanediol, glucose oxidase and lactoperoxidase, leuconostoc/radish root ferment filtrate, glyceryl laurate, benzoic acid esters, dihydroxamic acids, and acyl lactylates and glycol.

The amount of the antimicrobial agent(s) in the antimicrobial compositions is dependent on the relative amounts of other components present within the composition. For example, in some embodiments, the antimicrobial agent can be present in the compositions in an amount between about 0.001% to about 5% (by total weight of the composition), in some embodiments between about 0.01% to about 3% (by total weight of the composition), and in some embodiments, between about 0.01% to about 1.0% (by total weight of the composition). As used herein, the amount the antimicrobial agent provides in a composition is the active weight of the antimicrobial agent by total weight of the composition.

Antimicrobial Boosting Agents

The antimicrobial compositions of the present disclosure can also include one or more antimicrobial boosting agents. The antimicrobial boosting agent can include a sultaine. Through extensive testing, which will be described in greater detail below, it was surprisingly found that some sultaines can be used as a antimicrobial boosting agent to increase the effectiveness of an antimicrobial agent used in the antimicrobial composition. Sultaines are highly water soluble and have been previously utilized in compositions as a surfactant for their ability to help solubilize other composition ingredients, as well as for their ability to provide other surfactant properties, such as reducing surface tension. However, testing has revealed that certain sultaines can be extremely potent antimicrobial boosting agents, even when utilized at low concentrations, for example, such as providing less than 1.0% of the antimicrobial composition (by total weight of the composition), or even in some embodiments, providing less than 0.1% of the antimicrobial composition (by total weight of the composition). As such, some sultaines can provide a multifunctional ingredient for an antimicrobial composition, in that some sultaines can serve as an antimicrobial boosting agent configured to boost the effectiveness of the antimicrobial agent in the composition as well as acting as a surfactant to provide beneficial properties to the composition in that regard, such as reduced surface tension and to help solubility.

Initial testing was conducted to screen a variety of surfactants in researching for potential antimicrobial boosting agents. The initial testing followed the methodology as described in the Minimum Effective Concentration ("MEC") Test Method described in the Test Methods section herein. To summarize, the MEC testing paired a variety of potential antimicrobial boosting agents with a variety of known antimicrobial agents to determine the MEC of the respective antimicrobial agent that must be used to provide an effective antimicrobial result, as described in further detail in the Test Methods section. The more positive the boosting characteristics of an antimicrobial boosting agent, then the lower the MEC that would be required for the paired antimicrobial agent. Results of the MEC testing on some of the surfactants screened are shown in Table 1 below. It is to be noted that the molarities listed in Table 1 are approximate values that were calculated based on the estimated activities of the ingredients and the molecular weights of the active ingredients. In instances where an exact activity was not available for an ingredient blend, the ingredient blend activity was estimated as the average of the upper and lower limits of the specification provided by the manufacturer of such blend. In instances where an exact molecular weight could not be calculated (for example, in compounds derived from a natural oil like coconut oil), the molecular weight of the active was estimated based on a weighted average of the molecular weights of the constituent species.

TABLE 1

Minimum Effective Concentration Testing screening potential antimicrobial boosting agents.

| Potential Antimicrobial Boosting Agents | | | Antimicrobial Agents | | Results |
| --- | --- | --- | --- | --- | --- |
| Trade Name | INCI | Concentr. (mmol/L) | Trade Name | INCI | MEC (mmol/L) |
| None | None | N/A | Zeastat | Caprylhydroxamic Acid | 10 |
| Mackam LHS-E | Lauryl Hydroxysultaine | 5 | Zeastat | Caprylhydroxamic Acid | <2 |
| Tagat CH40 | PEG-40 Hydrogenated Castor Oil | 5 | Zeastat | Caprylhydroxamic Acid | 10 |
| Eumulgin SML-20 | Polysorbate 20 | 5 | Zeastat | Caprylhydroxamic Acid | 10 |
| ColaTeric CBS-HP | Cocamidopropyl Hydroxysultaine | 5 | Zeastat | Caprylhydroxamic Acid | Unstable |
| None | None | N/A | SymSave H | Hydroxyacetophenone | 20 |
| Mackam LHS-E | Lauryl Hydroxysultaine | 5 | SymSave H | Hydroxyacetophenone | <5 |
| 3-(Decyldimethyl-ammonio)-propane-sulfonate inner salt | Decyl Sultaine | 5 | SymSave H | Hydroxyacetophenone | 10 |
| N-Dodecyl-N,N-dimethyl-3-ammonio-1-propanesulfonate | Lauryl Sultaine | 5 | SymSave H | Hydroxyacetophenone | 10 |
| Cola Liquid DC | Cocamide DIPA | 5 | SymSave H | Hydroxyacetophenone | 20 |
| ColaTeric CBS-HP | Cocamidopropyl Hydroxysultaine | 5 | SymSave H | Hydroxyacetophenone | 20 |
| Tagat CH40 | PEG-40 Hydrogenated Castor Oil | 5 | SymSave H | Hydroxyacetophenone | >20 |
| Eumulgin SML-20 | Polysorbate 20 | 5 | SymSave H | Hydroxyacetophenone | >20 |
| None | None | N/A | Purac FCC 88 | Lactic Acid | 60 |
| Mackam LHS-E | Lauryl Hydroxysultaine | 5 | Purac FCC 88 | Lactic Acid | 17 |
| N-Dodecyl-N,N-dimethyl-3-ammonio-1-propanesulfonate | Lauryl Sultaine | 5 | Purac FCC 88 | Lactic Acid | 20 |
| 3-(Decyldimethyl-ammonio)-propane-sulfonate inner salt | Decyl Sultaine | 5 | Purac FCC 88 | Lactic Acid | 30 |

TABLE 1-continued

Minimum Effective Concentration Testing screening potential antimicrobial boosting agents.

| Potential Antimicrobial Boosting Agents | | | Antimicrobial Agents | | Results |
|---|---|---|---|---|---|
| Trade Name | INCI | Concentr. (mmol/L) | Trade Name | INCI | MEC (mmol/L) |
| ColaTeric CBS-HP | Cocamidopropyl Hydroxysultaine | 5 | Purac FCC 88 | Lactic Acid | 30 |
| Sopalteric LHS | Lauramidopropyl Hydroxysultaine | 5 | Purac FCC 88 | Lactic Acid | 30 |
| Dermosoft SLL | Sodium Lauroyl Lactylate | 5 | Purac FCC 88 | Lactic Acid | 30 |
| Plantaren 1200 NUP | Lauryl Glucoside | 5 | Purac FCC 88 | Lactic Acid | >30 |
| 3-(N,N-Dimethyl-myristylammonio)propanesulfonate | Myristyl Sultaine | 5 | Purac FCC 88 | Lactic Acid | 40 |
| 3-(Benzyldimethyl-ammonio)propane-sulfonate | Benzyl Sultaine | 5 | Purac FCC 88 | Lactic Acid | 40 |
| 3-(N,N-Dimethyl-octylammonio)propanesulfonate inner salt | Caprylyl Sultaine | 5 | Purac FCC 88 | Lactic Acid | 40 |
| Mackam CET | Cetyl Betaine | 5 | Purac FCC 88 | Lactic Acid | 40 |
| Mackanate Ultra Si | Disodium PEG-12 Dimethicone Sulfosuccinate | 5 | Purac FCC 88 | Lactic Acid | 40 |
| Dermalcare MAP L-130 | Laureth-3 Phosphate | 5 | Purac FCC 88 | Lactic Acid | 40 |
| Mackam BW-139 | Octyl Betaine | 5 | Purac FCC 88 | Lactic Acid | 40 |
| Techmine 280 | Octyldimethylamine Oxide | 5 | Purac FCC 88 | Lactic Acid | 40 |
| Cola Moist 200 | Hydroxypropyl Bis-Hydroxyethyldimonium Chloride | 5 | Purac FCC 88 | Lactic Acid | 50 |
| Alkamuls PSML-80/72LD | PEG-80 Sorbitan Laurate | 5 | Purac FCC 88 | Lactic Acid | 50 |
| Eumulgin SML-20 | Polysorbate 20 | 5 | Purac FCC 88 | Lactic Acid | 50 |
| Hostapon SCI 85 P | Sodium Cocoyl Isethionate | 5 | Purac FCC 88 | Lactic Acid | 50 |
| Suga Nate 160 | Sodium Laurylglucosides Hydroxypropylsulfonate | 5 | Purac FCC 88 | Lactic Acid | >50 |
| Plantaren 810 UP | Caprylyl/Capryl Glucoside | 5 | Purac FCC 88 | Lactic Acid | 60 |
| Plantacare 818 UP | Coco-Glucoside | 5 | Purac FCC 88 | Lactic Acid | >60 |
| Tagat CH40 | PEG-40 Hydrogenated Castor Oil | 5 | Purac FCC 88 | Lactic Acid | >60 |
| Cola Liquid DC | Cocamide DIPA | 5 | Purac FCC 88 | Lactic Acid | Unstable |
| None | None | N/A | Sodium Benzoate | Sodium Benzoate | 7.5 |
| Mackam LHS-E | Lauryl Hydroxysultaine | 5 | Sodium Benzoate | Sodium Benzoate | <1 |
| Hostapon CT Paste | Sodium Methyl Cocoyl Taurate | 5 | Sodium Benzoate | Sodium Benzoate | 2.5 |
| Eumulgin SML-20 | Polysorbate 20 | 5 | Sodium Benzoate | Sodium Benzoate | 5 |
| Plantaren 1200 NUP | Lauryl Glucoside | 5 | Sodium Benzoate | Sodium Benzoate | 10 |
| Dehyton PK-45 | Cocamidopropyl Betaine | 5 | Sodium Benzoate | Sodium Benzoate | >15 |

The results of the MEC testing shown in Table 1 provided some interesting principles. Some surfactants tested did not perform well as antimicrobial boosting agents, such as, PEG-40 Hydrogenated Castor Oil, Polysorbate 20, Sodium Cocoyl Isethionate, Coco-Glucoside, and Cocamide DIPA. Additionally, several different sultaines tested provided at least some antimicrobial boosting effect with at least one of the paired antimicrobial agents. These sultaines included: lauryl hydroxysultaine, decyl sultaine, lauryl sultaine, lauramidopropyl hydroxysultaine, myristyl sultaine, benzyl sultaine, capryl sultaine, and cocamidopropyl hydroxysultaine. However, from reviewing the screening results of the MEC testing, it was apparent that some of the sultaines provided more preferable antimicrobial boosting characteristics, such that the MEC of a paired antimicrobial agent could be significantly reduced, as well as more consistent antimicrobial boosting characteristics across use with various different antimicrobial agents. For example, lauryl hydroxysultaine, decyl sultaine, myristyl sultaine, and lauryl sultaine provided preferred antimicrobial boosting agents.

Figure 2:
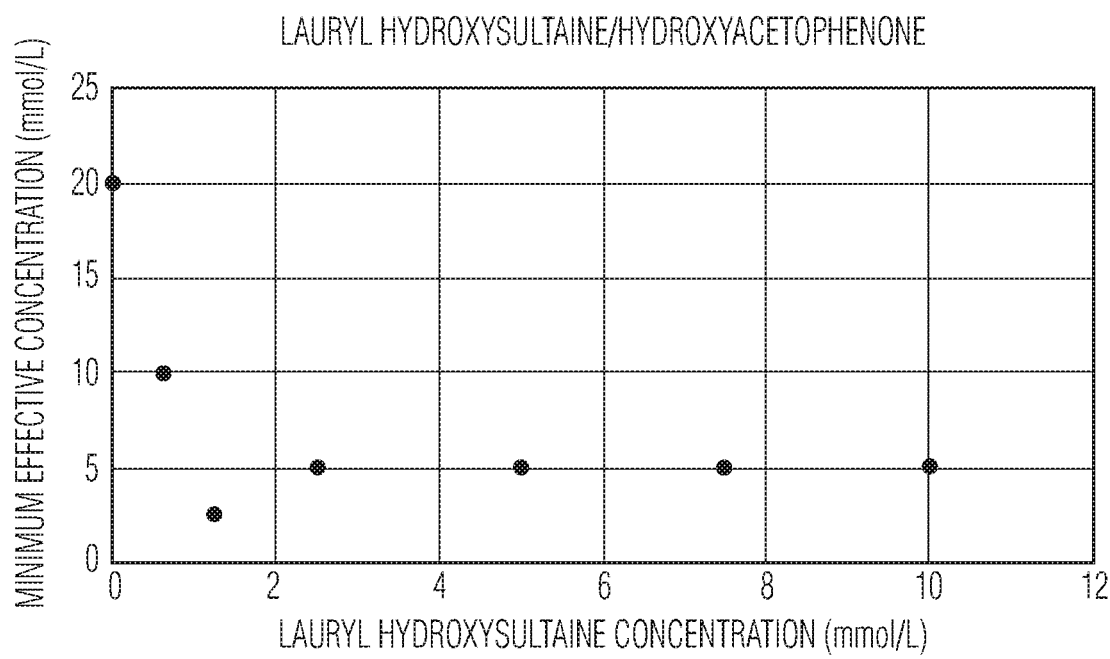
FIG. 2 displays a graph showing the results of MEC testing for a composition including the antimicrobial agent of hydroxyacetophenone and an antimicrobial agent of lauryl hydroxysultaine of varying concentrations of the antimicrobial boosting agent.

FIGS. 1 and 2 display another intriguing property regarding the antimicrobial compositions including an antimicrobial agent and an antimicrobial boosting agents including a sultaine. For example, FIG. 1 displays a graph showing the results of MEC testing similar to Table 1 above for a composition including the antimicrobial agent of lactic acid and an antimicrobial agent of lauryl hydroxysultaine. FIG. 2 displays a graph showing the results of MEC testing similar to Table 1 above for a composition including the antimicrobial agent of hydroxyacetophenone and an antimicrobial agent of lauryl hydroxysultaine. In both FIG. 1 and FIG. 2, the MEC data shows that increasing the concentration of the antimicrobial boosting agent does not lead to a linear decrease, or possibly even a decrease at all, in the minimum effective concentration of the antimicrobial agent required to provide a satisfactory antimicrobial effect defined by the Minimum Effective Concentration Test Method. Rather, the lowest minimum effective concentration of the antimicrobial agent required to provide a satisfactory antimicrobial effect initially reduces as the antimicrobial boosting agent is added in increasing concentration to the composition, but then the antimicrobial agent provides its most effective concentration when combined with a rather low concentration of the antimicrobial boosting agent. Providing a higher concentration of the antimicrobial boosting agent past that point either at best keeps the minimum effective concentration of the antimicrobial agent constant, or in some cases (such as in FIG. 1), may even increase such a minimum effective concentration of the antimicrobial agent required to provide a satisfactory antimicrobial effect. Thus, the antimicrobial boosting properties of an antimicrobial boosting agent may be at their maximum efficiency when the antimicrobial boosting agent is utilized in lower concentrations in an antimicrobial composition.

Additional testing was conducted on some of the sultaines providing antimicrobial boosting properties discovered in the initial screening process described above. This testing was conducted according to the Antimicrobial Efficacy Testing described in the Test Methods section herein, which focused on testing various antimicrobial boosting agents including a sultaine, and at varying concentrations, paired with various antimicrobial agents to determine their antimicrobial effectiveness against four different species of bacteria and two different species of fungi. As will be discussed further below, this testing focused not only on testing the effectiveness of antimicrobial compositions including an antimicrobial agent and an antimicrobial boosting agent, but also on such compositions applied to a substrate. The results of such testing, as well as discussion thereon, is noted below. For all compositions listed below, the composition ingredients were blended with deionized water and the pH of the resulting composition was checked. pH then was adjusted with HCl or NaOH solution to achieve a final pH of approximately 4.5, unless otherwise noted.

The antimicrobial agent of caprylhydroxamic acid, a non-aromatic compound, was the first antimicrobial agent tested in exemplary composition no. 1. Table 2 provides the result of the Antimicrobial Efficacy Testing as a control run of this antimicrobial agent. As shown in Table 2, the antimicrobial agent of caprylhydroxamic acid at a concentration of 6 mmol/L (0.10%) provides sufficient antimicrobial effectiveness by day 28 against all organisms, however, it does not provide quick, broad-spectrum effectiveness as it struggles against several organisms at day 7 including *C. albicans* and *A. brasiliensis*.

Exemplary Composition No. 1

Antimicrobial agent: caprylhydroxamic acid (Zeastat)
Antimicrobial agent concentration: 6 mmol/L
Antimicrobial agent blend weight %: 1.27%
Antimicrobial agent active weight %: 0.10%
Antimicrobial boosting agent: none

TABLE 2

Antimicrobial Efficacy Testing results for Exemplary Composition No. 1.

| Organism | Initial | Day 7 | Day 14 | Day 28 |
|---|---|---|---|---|
| | | CFU/gram or mL | | |
| S. aureus | 4.4E+05 | <1.0E+01 | <1.0E+01 | <1.0E+01 |
| E. coli | 5.8E+05 | <1.0E+01 | <1.0E+01 | <1.0E+01 |
| P. aeruginosa | 3.2E+05 | <1.0E+01 | <1.0E+01 | <1.0E+01 |
| C. albicans | 3.8E+05 | >2.5e+03 | <1.0E+01 | <1.0E+01 |
| A. brasiliensis | 6.8E+05 | 4.0E+04 | 9.5E+02 | <1.0E+02 |
| B. cepacia | 2.8E+05 | <1.0E+01 | <1.0E+01 | <1.0E+01 |

Table 3 provides a control run of the testing of the antimicrobial boosting agent lauryl hydroxysultaine. As seen from reviewing the results of the Antimicrobial Efficacy Testing in Table 3, the antimicrobial boosting agent of lauryl hydroxysultaine does not provide a broad class antimicrobial effect in composition by itself. Particularly, the lauryl hydroxysultaine did not provide a satisfactory antimicrobial effect against *B. cepacia*.

Exemplary Composition No. 2

Antimicrobial agent: none
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%

TABLE 3

Antimicrobial Efficacy Testing results for Exemplary Composition No. 2.

| Organism | Initial | Day 7 | Day 14 | Day 28 |
|---|---|---|---|---|
| | | CFU/gram or mL | | |
| S. aureus | 1.5E+05 | <1.0E+01 | <1.0E+01 | <1.0E+01 |
| E. coli | 2.2E+05 | <1.0E+01 | <1.0E+01 | <1.0E+01 |
| P. aeruginosa | 1.8E+05 | <1.0E+01 | <1.0E+01 | <1.0E+01 |
| C. albicans | 2.0E+05 | <1.0E+01 | <1.0E+01 | <1.0E+01 |
| A. brasiliensis | 2.0E+05 | 9.0E+02 | 3.0E+02 | <1.0E+02 |
| B. cepacia | 1.4E+05 | 1.4E+04 | 1.7E+04 | 8.6E+03 |

Table 4 provides the testing results of exemplary composition no. 3 which employs the antimicrobial agent of caprylhydroxamic acid along with the antimicrobial boosting agent of lauryl hydroxysultaine. This composition was not stable overnight, and thus, N/S is listed in each category of testing to denote no results were documented due to the lack of stability. Thus, it was demonstrated that not any antimicrobial boosting agent including a sultaine can be combined with any antimicrobial agent and still provide a stable formulation.

Exemplary Composition No. 3

Antimicrobial agent: caprylhydroxamic acid (Zeastat)
Antimicrobial agent concentration: 6 mmol/L
Antimicrobial agent blend weight %: 1.27%
Antimicrobial agent active weight %: 0.10%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%

TABLE 4

Antimicrobial Efficacy Testing results for Exemplary Composition No. 3.

| Organism | Initial | Day 7 | Day 14 | Day 28 |
|---|---|---|---|---|
| | | CFU/gram or mL | | |
| S. aureus | N/S | N/S | N/S | N/S |
| E. coli | N/S | N/S | N/S | N/S |
| P. aeruginosa | N/S | N/S | N/S | N/S |
| C. albicans | N/S | N/S | N/S | N/S |
| A. brasiliensis | N/S | N/S | N/S | N/S |
| B. cepacia | N/S | N/S | N/S | N/S |

The next antimicrobial agent that was tested was hydroxyacetophenone, an aromatic compound. Exemplary composition no. 4 provided a control run for this antimicrobial agent at a 10 mmol/L concentration without any antimicrobial boosting agent, and the results are shown in Table 5. As shown from the results in Table 5, this antimicrobial agent did not provide quick, broad-spectrum antimicrobial effectiveness, as several organisms survived through Day 7, including *C. albicans*, *A. brasiliensis*, and *B. cepacia*.

Exemplary Composition No. 4

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: None

TABLE 5

Antimicrobial Efficacy Testing results for Exemplary Composition No. 4.

| Organism | Initial | Day 7 | Day 14 | Day 28 |
|---|---|---|---|---|
| | | CFU/gram or mL | | |
| S. aureus | 1.7E+05 | <1.0E+01 | <1.0E+01 | <1.0E+01 |
| E. coli | 3.0E+05 | <1.0E+01 | <1.0E+01 | <1.0E+01 |
| P. aeruginosa | 2.0E+05 | <1.0E+01 | <1.0E+01 | <1.0E+01 |
| C. albicans | 3.0E+05 | 1.3E+04 | 1.1E+04 | 2.6E+03 |
| A. brasiliensis | 2.8E+05 | 7.0E+04 | 5.5E+04 | 6.0E+04 |
| B. cepacia | 1.6E+05 | 3.5E+01 | <1.0E+01 | <1.0E+01 |

Exemplary compositions nos. 5 and 6 tested the antimicrobial agent of hydroxyacetophenone with two different concentrations of the antimicrobial boosting agent of lauryl hydroxysultaine (results shown in Tables 6 and 7). Exemplary compositions nos. 5 and 6 were only tested through Day 7 and were not completed against organisms of *E. coli* and *P. aeruginosa* (cells not tested marked as "N/T"). As shown from the results in Tables 6 and 7, the antimicrobial boosting agent of lauryl hydroxysultaine used along with the antimicrobial agent of hydroxyacetophenone provided an increase in antimicrobial effectiveness against *C. albicans*, *A. brasiliensis*, and *B. cepacia* compared to exemplary composition no. 4 that only included the antimicrobial agent of hydroxyacetophenone. Because the composition no. 2 (Table 3) described above that employed lauryl hydroxysultaine by itself failed to provide a satisfactory antimicrobial effectiveness against *A. brasiliensis* or *B. cepacia*, the combination of the antimicrobial agent of hydroxyacetophenone and the antimicrobial boosting agent of lauryl hydroxysultaine demonstrated surprising synergistic results.

Exemplary Composition No. 5

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%

TABLE 6

Antimicrobial Efficacy Testing results for Exemplary Composition No. 5.

| Organism | Initial | Day 7 | Day 14 | Day 28 |
|---|---|---|---|---|
| | | CFU/gram or mL | | |
| S. aureus | 1.5E+05 | <1.0E+01 | <1.0E+01 | <1.0E+01 |
| E. coli | 2.2E+05 | <1.0E+01 | <1.0E+01 | <1.0E+01 |
| P. aeruginosa | 1.8E+05 | <1.0E+01 | <1.0E+01 | <1.0E+01 |
| C. albicans | 2.0E+05 | <1.0E+01 | <1.0E+01 | <1.0E+01 |
| A. brasiliensis | 2.0E+05 | <1.0E+02 | <1.0E+02 | <1.0E+02 |
| B. cepacia | 1.4E+05 | <1.0E+01 | <1.0E+01 | <1.0E+01 |

Exemplary Composition No. 6

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: lauryl hydroxysultaine (Mackam LHS-E)
Antimicrobial boosting agent concentration: 2.5 mmol/L
Antimicrobial boosting agent blend weight %: 0.187%
Antimicrobial boosting agent active weight %: 0.09%

TABLE 7

Antimicrobial Efficacy Testing results for Exemplary Composition No. 6.

| Organism | Initial | Day 7 | Day 14 | Day 28 |
|---|---|---|---|---|
| | | CFU/gram or mL | | |
| S. aureus | 3.4E+05 | <1.0E+01 | N/T | N/T |
| E. coli | N/T | N/T | N/T | N/T |
| P. aeruginosa | N/T | N/T | N/T | N/T |
| C. albicans | 4.7E+05 | <1.0E+01 | N/T | N/T |
| A. brasiliensis | 4.3E+05 | <1.0E+02 | N/T | N/T |
| B. cepacia | 3.0E+05 | <1.0E+01 | N/T | N/T |

Testing was also conducted against the antimicrobial agent of hydroxyacetophenone at a concentration of 7.5 mmol/L. Exemplary composition no. 7 was a control run of this antimicrobial agent at this concentration level and is shown in Table 8. This antimicrobial agent at this concentration level was tested along with the antimicrobial boosting agent of lauryl hydroxysultaine in exemplary composition no. 8 in Table 9. As shown from Tables 8 and 9, improvement against *S. aureus*, *E. coli*, *C. albicans*, *A. brasiliensis*, and *B. cepacia* was demonstrated by the combination of the antimicrobial agent of hydroxyacetophenone at a concentration of 7.5 mmol/L (0.10% weight) used along with the antimicrobial boosting agent of lauryl hydroxysultaine. As mentioned above, because the composition no. 2 (Table 3) that employed lauryl hydroxysultaine by itself failed to provide a satisfactory antimicrobial effectiveness against *A. brasiliensis* or *B. cepacia*, the combination of the antimicrobial agent of hydroxyacetophenone and the antimicrobial boosting agent of lauryl hydroxysultaine demonstrated synergistic results.

Exemplary Composition No. 7

Antimicrobial agent: hydroxyacetophenone (Symsave H)
Antimicrobial agent concentration: 7.5 mmol/L
Antimicrobial agent blend weight %: 0.10%
Antimicrobial agent active weight %: 0.10%
Antimicrobial boosting agent: None

TABLE 8

Antimicrobial Efficacy Testing results for Exemplary Composition No. 7.

| Organism | Initial | Day 7 | Day 14 | Day 28 |
|---|---|---|---|---|
| | | CFU/gram or mL | | |
| S. aureus | 4.4E+05 | >2.5E+03 | <1.0E+01 | <1.0E+01 |
| E. coli | 5.8E+05 | 7.4E+02 | <1.0E+01 | <1.0E+01 |
| P. aeruginosa | 3.2E+05 | <1.0E+01 | <1.0E+01 | <1.0E+01 |
| C. albicans | 3.8E+05 | >2.5E+03 | >2.5E+05 | 1.1E+05 |
| A. brasiliensis | 6.8E+05 | >8.0E+04 | 4.5E+05 | 8.0E+04 |
| B. cepacia | 2.8E+05 | >2.5E+03 | >2.5E+05 | 7.6E+04 |

Exemplary Composition No. 8

Antimicrobial agent: hydroxyacetophenone (Symsave H)
Antimicrobial agent concentration: 7.5 mmol/L
Antimicrobial agent blend weight %: 0.10%
Antimicrobial agent active weight %: 0.10%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%

TABLE 9

Antimicrobial Efficacy Testing results for Exemplary Composition No. 8.

| Organism | Initial | Day 7 | Day 14 | Day 28 |
|---|---|---|---|---|
| | | CFU/gram or mL | | |
| S. aureus | 4.4E+05 | <1.0E+01 | <1.0E+01 | <1.0E+01 |
| E. coli | 5.8E+05 | <1.0E+01 | <1.0E+01 | <1.0E+01 |
| P. aeruginosa | 3.2E+05 | <1.0E+01 | <1.0E+01 | <1.0E+01 |
| C. albicans | 3.8E+05 | <1.0E+01 | <1.0E+01 | <1.0E+01 |
| A. brasiliensis | 6.8E+05 | <1.0E+02 | <1.0E+02 | <1.0E+02 |
| B. cepacia | 2.8E+05 | <1.0E+01 | <1.0E+01 | <1.0E+01 |

The antimicrobial boosting agent of hydroxyacetophenone was tested at an even further reduced concentration of 5.0 mmol/L. Exemplary composition no. 9 was a control run of this antimicrobial agent at this concentration level and is shown in Table 10. This antimicrobial agent at this concentration level was tested along with the antimicrobial boosting agent of lauryl hydroxysultaine at two different concentrations. Exemplary composition no. 10 (Table 11) and exemplary composition no. 11 (Table 12) had the antimicrobial agent of hydroxyacetophenone at a concentration of 5.0 mmol/L and the antimicrobial boosting agent of lauryl hydroxysultaine being at a concentration of 5 mmol/L (0.18%) and 2.5 mmol/L (0.09%), respectively. As shown in the Tables 10-12, the combination of the antimicrobial agent of hydroxyacetophenone and the antimicrobial boosting agent of lauryl hydroxysultaine (in either concentration) provided improved antimicrobial effectiveness against *S. aureus*, *C. albicans*, *A. brasiliensis*, and *B. cepacia*. The improved antimicrobial effectiveness against *A. brasiliensis* or *B. cepacia* is especially surprising due to the synergistic results described above for lauryl hydroxysultaine.

Exemplary Composition No. 9

Antimicrobial agent: hydroxyacetophenone (Symsave H)
Antimicrobial agent concentration: 5.0 mmol/L
Antimicrobial agent blend weight %: 0.07%
Antimicrobial agent active weight %: 0.07%
Antimicrobial boosting agent: None

TABLE 10

Antimicrobial Efficacy Testing results for Exemplary Composition No. 9.

| Organism | Initial | Day 7 | Day 14 | Day 28 |
|---|---|---|---|---|
| | | CFU/gram or mL | | |
| S. aureus | 3.4E+05 | >2.5E+03 | N/T | N/T |
| E. coli | N/T | N/T | N/T | N/T |
| P. aeruginosa | N/T | N/T | N/T | N/T |
| C. albicans | 4.7E+05 | >2.5E+04 | N/T | N/T |
| A. brasiliensis | 4.3E+05 | 8.5E+04 | N/T | N/T |
| B. cepacia | 3.0E+05 | >2.5E+03 | N/T | N/T |

Exemplary Composition No. 10

Antimicrobial agent: hydroxyacetophenone (Symsave H)
Antimicrobial agent concentration: 5.0 mmol/L
Antimicrobial agent blend weight %: 0.07%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%

TABLE 11

Antimicrobial Efficacy Testing results for Exemplary Composition No. 10.

| Organism | Initial | Day 7 | Day 14 | Day 28 |
|---|---|---|---|---|
| | | CFU/gram or mL | | |
| S. aureus | 3.4E+05 | <1.0E+01 | N/T | N/T |
| E. coli | N/T | N/T | N/T | N/T |
| P. aeruginosa | N/T | N/T | N/T | N/T |
| C. albicans | 4.7E+05 | <1.0E+01 | N/T | N/T |
| A. brasiliensis | 4.3E+05 | 2.0E+02 | N/T | N/T |
| B. cepacia | 3.0E+05 | <1.0E+01 | N/T | N/T |

Exemplary Composition No. 11

Antimicrobial agent: hydroxyacetophenone (Symsave H)
Antimicrobial agent concentration: 5.0 mmol/L
Antimicrobial agent blend weight %: 0.07%
Antimicrobial agent active weight %: 0.07%
Antimicrobial boosting agent: lauryl hydroxysultaine (Mackam LHS-E)
Antimicrobial boosting agent concentration: 2.5 mmol/L
Antimicrobial boosting agent blend weight %: 0.19%
Antimicrobial boosting agent active weight %: 0.09%

TABLE 12

Antimicrobial Efficacy Testing results for Exemplary Composition No. 11.

| Organism | Initial | Day 7 | Day 14 | Day 28 |
|---|---|---|---|---|
| | | CFU/gram or mL | | |
| S. aureus | 3.4E+05 | <1.0E+01 | N/T | N/T |
| E. coli | N/T | N/T | N/T | N/T |
| P. aeruginosa | N/T | N/T | N/T | N/T |
| C. albicans | 4.7E+05 | <1.0E+01 | N/T | N/T |
| A. brasiliensis | 4.3E+05 | 1.0E+02 | N/T | N/T |
| B. cepacia | 3.0E+05 | <1.0E+01 | N/T | N/T |

Yet another antimicrobial agent, sodium benzoate, was tested in Antimicrobial Efficacy Testing with various antimicrobial boosting agents including a sultaine. Sodium benzoate is an aromatic organic acid. This testing involved first testing of sodium benzoate in a control run at a concentration of 3.5 mmol/L (0.05%) without any antimicrobial boosting agent in composition no. 12. As shown from the results in Table 13, this antimicrobial agent did not provide satisfactory antimicrobial effectiveness against *B. cepacia*, and only marginal results against *C. albicans* and *A. brasiliensis*.

Exemplary Composition No. 12

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: None

TABLE 13

Antimicrobial Efficacy Testing results for Exemplary Composition No. 12.

| Organism | Initial | Day 7 | Day 14 | Day 28 |
|---|---|---|---|---|
| | | CFU/gram or mL | | |
| S. aureus | 1.5E+05 | <1.0E+01 | <1.0E+01 | <1.0E+01 |
| E. coli | 2.2E+05 | <1.0E+01 | <1.0E+01 | <1.0E+01 |
| P. aeruginosa | 1.8E+05 | <1.0E+01 | <1.0E+01 | <1.0E+01 |
| C. albicans | 2.0E+05 | >2.5E+04 | 4.0E+03 | <1.0E+01 |
| A. brasiliensis | 2.0E+05 | 3.6E+04 | 8.0E+04 | 7.1E+05 |
| B. cepacia | 1.4E+05 | 8.0E+01 | 6.0E+02 | 8.1E+04 |

The antimicrobial agent of sodium benzoate at 3.5 mmol/L (0.05%) was tested in combination with several different antimicrobial boosting agents including a sultaine. The sodium benzoate was tested with the antimicrobial boosting agent of caprylyl sultaine in exemplary composition no. 13 at a concentration of 5 mmol/L (0.14%) and also with the antimicrobial boosting agent of myristyl sultaine in exemplary composition no. 14 at a concentration of 5 mmol/L (0.18%). Sodium benzoate was also tested with the antimicrobial boosting agent of lauryl hydroxysultaine at concentrations of 8.6 mmol/L (composition no. 15) and 5 mmol/L (composition no. 16). As shown in the results of Table 14, the antimicrobial boosting agent of caprylyl sultaine in combination with the antimicrobial agent of sodium benzoate failed to provide satisfactory antimicrobial effectiveness against *A. brasiliensis* and *B. cepacia*, providing minimal boosting effect to the antimicrobial agent of sodium benzoate. In addition, the caprylyl sultaine in combination with the sodium benzoate actually provided a negative effect against *C. albicans* in comparison to the use of sodium benzoate alone (composition 12—Table 13).

However, the antimicrobial boosting agents of myristyl sultaine and lauryl hydroxysultaine provided improvements in antimicrobial effectiveness. For example, as shown in Table 15, the antimicrobial boosting agent of myristyl sultaine combined with the antimicrobial agent of sodium benzoate provided an increase in antimicrobial effectiveness against *C. albicans*, *A. brasiliensis*, and *B. cepacia* as compared to the use of the antimicrobial agent of sodium benzoate alone (composition no. 12—Table 13). Similarly, as shown in the results of Tables 16 and 17, the antimicrobial boosting agent of lauryl hydroxysultaine also provided an improvement in antimicrobial effectiveness against *C. albicans*, *A. brasiliensis*, and *B. cepacia* as compared to the use of the antimicrobial agent of sodium benzoate alone (composition no. 12—Table 13). As noted above regarding the antimicrobial boosting agent of lauryl hydroxysultaine, the results of the combination of the antimicrobial agent of sodium benzoate and the antimicrobial boosting agent of lauryl hydroxysultaine against *A. brasiliensis* or *B. cepacia* are particularly surprising in that the use of lauryl hydroxysultaine by itself (composition no. 2—Table 3) was not effective against *A. brasiliensis* or *B. cepacia*. Thus, the results of this Antimicrobial Efficacy Testing including sodium benzoate showed that some antimicrobial agents are sensitive to different sultaines as antimicrobial boosting agents, and some synergistic results can be achieved by selecting proper combinations of antimicrobial agents and antimicrobial boosting agents including sultaines.

Exemplary Composition No. 13

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: caprylyl sultaine (3-(N,N-dimethyloctylammonio)propanesulfonate inner salt)
Antimicrobial boosting agent concentration: 5.0 mmol/L
Antimicrobial boosting agent blend weight %: 0.14%
Antimicrobial boosting agent active weight %: 0.14%

TABLE 14

Antimicrobial Efficacy Testing results for Exemplary Composition No. 13.

| Organism | Initial | Day 7 | Day 14 | Day 28 |
|---|---|---|---|---|
| | | CFU/gram or mL | | |
| S. aureus | 4.4E+05 | 2.0E+01 | <1.0E+01 | <1.0E+01 |
| E. coli | 5.8E+05 | 1.0E+01 | <1.0E+01 | <1.0E+01 |
| P. aeruginosa | 3.2E+05 | <1.0E+01 | <1.0E+01 | <1.0E+01 |
| C. albicans | 3.8E+05 | >2.5E+03 | 1.1E+05 | 3.7E+03 |
| A. brasiliensis | 6.8E+05 | 5.2E+04 | 4.8E+04 | 3.4E+04 |
| B. cepacia | 2.8E+05 | <1.0E+01 | 6.0E+02 | >2.5E+04 |

Exemplary Composition No. 14

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: myristyl sultaine (3-(N,N-Dimethylmyristylammonio)propanesulfonate)
Antimicrobial boosting agent concentration: 5.0 mmol/L
Antimicrobial boosting agent blend weight %: 0.18%
Antimicrobial boosting agent active weight %: 0.18%

TABLE 15

Antimicrobial Efficacy Testing results for Exemplary Composition No. 14.

| Organism | Initial | Day 7 | Day 14 | Day 28 |
|---|---|---|---|---|
| | | CFU/gram or mL | | |
| S. aureus | 4.4E+05 | <1.0E+01 | <1.0E+01 | <1.0E+01 |
| E. coli | 5.8E+05 | <1.0E+01 | <1.0E+01 | <1.0E+01 |
| P. aeruginosa | 3.2E+05 | <1.0E+01 | <1.0E+01 | <1.0E+01 |
| C. albicans | 3.8E+05 | <1.0E+01 | <1.0E+01 | <1.0E+01 |
| A. brasiliensis | 6.8E+05 | <1.0E+02 | <1.0E+02 | <1.0E+02 |
| B. cepacia | 2.8E+05 | <1.0E+01 | <1.0E+01 | <1.0E+01 |

Exemplary Composition No. 15

Antimicrobial agent: sodium benzoate
Antimicrobial agent concentration: 3.5 mmol/L
Antimicrobial agent blend weight %: 0.05%

Antimicrobial agent active weight %: 0.05%
Antimicrobial boosting agent: lauryl hydroxysultaine (Mackam LHS-E)
Antimicrobial boosting agent concentration: 8.6 mmol/L
Antimicrobial boosting agent blend weight %: 0.64%
Antimicrobial boosting agent active weight %: 0.30%

TABLE 16

Antimicrobial Efficacy Testing results for Exemplary Composition No. 15.

| Organism | Initial | Day 7 | Day 14 | Day 28 |
|---|---|---|---|---|
|  |  | CFU/gram or mL |  |  |
| S. aureus | 2.9E+05 | <1.0E+01 | <1.0E+01 | <1.0E+01 |
| E. coli | 5.2E+05 | <1.0E+01 | <1.0E+01 | <1.0E+01 |
| P. aeruginosa | 3.4E+05 | <1.0E+01 | <1.0E+01 | <1.0E+01 |
| C. albicans | 4.5E+05 | 5.0E+00 | <1.0E+01 | <1.0E+01 |
| A. brasiliensis | 4.5E+05 | <1.0E+02 | <1.0E+02 | <1.0E+02 |
| B. cepacia | 3.4E+05 | <1.0E+01 | <1.0E+01 | <1.0E+01 |

Exemplary Composition No. 16

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: lauryl hydroxysultaine (Mackam LHS-E)
Antimicrobial boosting agent concentration: 5.0 mmol/L
Antimicrobial boosting agent blend weight %: 0.37%
Antimicrobial boosting agent active weight %: 0.18%

TABLE 17

Antimicrobial Efficacy Testing results for Exemplary Composition No. 16.

| Organism | Initial | Day 7 | Day 14 | Day 28 |
|---|---|---|---|---|
|  |  | CFU/gram or mL |  |  |
| S. aureus | 1.7E+05 | <1.0E+01 | <1.0E+01 | <1.0E+01 |
| E. coli | 3.0E+05 | <1.0E+01 | <1.0E+01 | <1.0E+01 |
| P. aeruginosa | 2.0E+05 | <1.0E+01 | <1.0E+01 | <1.0E+01 |
| C. albicans | 3.0E+05 | <1.0E+01 | <1.0E+01 | <1.0E+01 |
| A. brasiliensis | 2.8E+05 | <1.0E+02 | <1.0E+02 | <1.0E+02 |
| B. cepacia | 1.6E+05 | <1.0E+01 | <1.0E+01 | <1.0E+01 |

The antimicrobial agent of sodium benzoate was also tested against other surfactants that could potentially serve as an antimicrobial boosting agent, such as lauryl glucoside in exemplary composition no. 17 and sodium methyl cocoyl taurate in exemplary composition no. 18. As shown from the results in Table 18, the combination of the antimicrobial agent of sodium benzoate and the lauryl glucoside did not provide a satisfactory increase in the antimicrobial performance of sodium benzoate against the compounds of C. albicans or A. brasiliensis, and decreased the antimicrobial effectiveness of sodium benzoate against B. cepacia. As shown in the results of Table 19, however, the combination of the antimicrobial agent of sodium benzoate and sodium methyl cocoyl taurate (composition 18) did improve the antimicrobial effectiveness of sodium benzoate against C. albicans, A. brasiliensis, and B. cepacia.

Exemplary Composition No. 17

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: lauryl glucoside (Plantaren 1200 N UP)
Antimicrobial boosting agent concentration: 5.0 mmol/L
Antimicrobial boosting agent blend weight %: 0.34%
Antimicrobial boosting agent active weight %: 0.17%

TABLE 18

Antimicrobial Efficacy Testing results for Exemplary Composition No. 17.

| Organism | Initial | Day 7 | Day 14 | Day 28 |
|---|---|---|---|---|
|  |  | CFU/gram or mL |  |  |
| S. aureus | 4.4E+05 | <1.0E+01 | <1.0E+01 | <1.0E+01 |
| E. coli | 5.8E+05 | <1.0E+01 | <1.0E+01 | <1.0E+01 |
| P. aeruginosa | 3.2E+05 | <1.0E+01 | <1.0E+01 | <1.0E+01 |
| C. albicans | 3.8E+05 | >2.5E+03 | 9.3E+03 | 2.0E+01 |
| A. brasiliensis | 6.8E+05 | 1.5E+04 | 1.8E+04 | 4.8E+03 |
| B. cepacia | 2.8E+05 | >2.5E+03 | >2.5E+05 | >2.5E+05 |

Exemplary Composition No. 18

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: sodium methyl cocoyl taurate (Hostapon CT Paste)
Antimicrobial boosting agent concentration: 8.9 mmol/L
Antimicrobial boosting agent blend weight %: 1.00%
Antimicrobial boosting agent active weight %: 1.00%

TABLE 19

Antimicrobial Efficacy Testing results for Exemplary Composition No. 18.

| Organism | Initial | Day 7 | Day 14 | Day 28 |
|---|---|---|---|---|
|  |  | CFU/gram or mL |  |  |
| S. aureus | 1.7E+05 | <1.0E+01 | <1.0E+01 | <1.0E+01 |
| E. coli | 3.0E+05 | <1.0E+01 | <1.0E+01 | <1.0E+01 |
| P. aeruginosa | 2.0E+05 | <1.0E+01 | <1.0E+01 | <1.0E+01 |
| C. albicans | 3.0E+05 | 3.0E+03 | <1.0E+01 | <1.0E+01 |
| A. brasiliensis | 2.8E+05 | 1.5E+02 | 1.0E+02 | <1.0E+02 |
| B. cepacia | 1.6E+05 | <1.0E+01 | <1.0E+01 | <1.0E+01 |

Sodium benzoate was also tested by itself in significantly higher concentrations to see if its antimicrobial effectiveness could be enhanced without any boosting agent. Compositions 19 and 20 below tested sodium benzoate at concentrations of 10.5 mmol/L (0.15%) and 17.5 mmol/L (0.25%), respectively. As shown in Tables 20 and 21, increasing the concentration of the antimicrobial agent of sodium benzoate in comparison to the 3.5 mmol/L (0.05%) as was used in composition 12 (Table 13) did provide for an increase in antimicrobial effectiveness against C. albicans, A brasiliensis, and B. cepacia. However, increasing the compositional percentage that the antimicrobial agent has in the formulation has many drawbacks as previously noted, such as, lowering the water content of the formulation and increasing malodor, making the formulation less appealing to consumers. Increasing the antimicrobial agent concentration in the formulation also increases formulation cost, whereas including an antimicrobial boosting agent typically has lower impact on product cost since it can serve dual roles as both a surfactant and antimicrobial boosting agent.

Exemplary Composition No. 19

Antimicrobial agent: sodium benzoate
Antimicrobial agent concentration: 10.5 mmol/L
Antimicrobial agent blend weight %: 0.15%
Antimicrobial agent active weight %: 0.15%
Antimicrobial boosting agent: None

TABLE 20

Antimicrobial Efficacy Testing results for Exemplary Composition No. 19.

| Organism | Initial | Day 7 | Day 14 | Day 28 |
|---|---|---|---|---|
| | | CFU/gram or mL | | |
| S. aureus | 1.7E+05 | <1.0E+01 | <1.0E+01 | <1.0E+01 |
| E. coli | 3.0E+05 | <1.0E+01 | <1.0E+01 | <1.0E+01 |
| P. aeruginosa | 2.0E+05 | <1.0E+01 | <1.0E+01 | <1.0E+01 |
| C. albicans | 3.0E+05 | 3.7E+02 | <1.0E+01 | <1.0E+01 |
| A. brasiliensis | 2.8E+05 | 2.0E+02 | 1.5E+02 | 2.0E+02 |
| B. cepacia | 1.6E+05 | <1.0E+01 | <1.0E+01 | <1.0E+01 |

Exemplary Composition No. 20

Antimicrobial agent: sodium benzoate
Antimicrobial agent concentration: 17.5 mmol/L
Antimicrobial agent blend weight %: 0.25%
Antimicrobial agent active weight %: 0.25%
Antimicrobial boosting agent: None

TABLE 21

Antimicrobial Efficacy Testing results for Exemplary Composition No. 20.

| Organism | Initial | Day 7 | Day 14 | Day 28 |
|---|---|---|---|---|
| | | CFU/gram or mL | | |
| S. aureus | 1.7E+05 | <1.0E+01 | <1.0E+01 | <1.0E+01 |
| E. coli | 3.0E+05 | <1.0E+01 | <1.0E+01 | <1.0E+01 |
| P. aeruginosa | 2.0E+05 | <1.0E+01 | <1.0E+01 | <1.0E+01 |
| C. albicans | 3.0E+05 | <1.0E+01 | <1.0E+01 | <1.0E+01 |
| A. brasiliensis | 2.8E+05 | <1.0E+02 | <1.0E+02 | <1.0E+02 |
| B. cepacia | 1.6E+05 | <1.0E+01 | <1.0E+01 | <1.0E+01 |

Antimicrobial Efficacy Testing was also completed with the use of various compositions on a substrate. The first substrate that was tested was a coform substrate, which is a composite of a matrix of meltblown fibers and an absorbent material (e.g., pulp fibers). Such substrates have been used as an absorbent layer in a wide variety of applications, including, but not limited to, absorbent articles, absorbent dry wipes, wet wipes, and mops. The testing of exemplary compositions on coform substrates was completed by applying the exemplary compositions at a rate of 3.3 grams of formulation per gram of dry basesheet to a substrate of coform with a basis weight of 64 g/m².

Exemplary composition no. 4 (Table 5) described above including an antimicrobial agent of hydroxyacetophenone at a 10 mmol/L concentration (0.14%) with no antimicrobial boosting agent was applied to the coform substrate as described above. The results are shown in Table 23 and demonstrate similar deficiencies in antimicrobial performance as were seen in Table 5 against C. albicans and A. brasiliensis, but also unsatisfactory antimicrobial efficacy against B. cepacia and slow efficacy against E. coli.

Exemplary Composition No. 4 on Substrate

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: None
Substrate: coform

TABLE 22

Antimicrobial Efficacy Testing results for Exemplary Composition No. 4 on a coform substrate.

| Organism | Initial | Day 7 | Day 14 | Day 28 |
|---|---|---|---|---|
| | | CFU/gram or mL | | |
| S. aureus | 9.5E+05 | <1.0E+01 | <1.0E+01 | <1.0E+01 |
| E. coli | 1.5E+06 | 3.9E+03 | <1.0E+01 | <1.0E+01 |
| P. aeruginosa | 8.9E+05 | <1.0E+01 | <1.0E+01 | <1.0E+01 |
| C. albicans | 8.4E+05 | >2.5E+04 | 2.3E+05 | 1.7E+04 |
| A. brasiliensis | 1.1E+06 | 3.0E+04 | 7.5E+04 | 5.0E+04 |
| B. cepacia | 1.2E+06 | >2.5E+04 | >2.5E+05 | >2.5E+05 |

Exemplary composition no. 2 including the antimicrobial boosting agent of lauryl hydroxysultaine at a concentration of 5 mmol/L (0.18%), but no antimicrobial agent, was also applied to a substrate of coform and tested and the results are shown in Table 23. As shown in Table 23, exemplary composition no. 2 demonstrated unsatisfactory antimicrobial efficiency against A. brasiliensis and B. cepacia as demonstrated in Table 3, but also demonstrated poor antimicrobial efficiency against E. coli and C. albicans when tested on coform.

Exemplary Composition No. 2 on Substrate

Antimicrobial agent: none
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%
Substrate: coform

TABLE 23

Antimicrobial Efficacy Testing results for Exemplary Composition No. 2 on a coform substrate.

| Organism | Initial | Day 7 | Day 14 | Day 28 |
|---|---|---|---|---|
| | | CFU/gram or mL | | |
| S. aureus | 9.5E+05 | <1.0E+01 | <1.0E+01 | <1.0E+01 |
| E. coli | 1.5E+06 | 3.1E+03 | <1.0E+01 | 2.2E+02 |
| P. aeruginosa | 8.9E+05 | <1.0E+01 | <1.0E+01 | <1.0E+01 |
| C. albicans | 8.4E+05 | 2.3E+02 | 4.0E+01 | 2.9E+04 |
| A. brasiliensis | 1.1E+06 | 4.0E+04 | 2.6E+04 | 1.1E+05 |
| B. cepacia | 1.2E+06 | >2.5E+04 | 2.5E+05 | 2.5E+05 |

Exemplary composition no. 5 including the antimicrobial agent of hydroxyacetophenone at 10 mmol/L concentration (0.14%) and antimicrobial boosting agent lauryl hydroxysultaine at a concentration of 5 mmol/L (0.18%) was applied to a substrate of coform and tested for antimicrobial efficacy. The results are shown in Table 24 below and demonstrate that the antimicrobial boosting agent of lauryl hydroxysultaine increased the antimicrobial efficacy of the antimicrobial agent of hydroxyacetophenone against E. coli, C. albicans, A. brasiliensis, and B. cepacia.

Exemplary Composition No. 5 on Substrate

Antimicrobial agent: hydroxyacetophenone (Symsave H)
Antimicrobial agent concentration: 10 mmol/L Antimicrobial agent blend weight %: 0.14%
Antimicrobial agent active weight %: 0.14%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%
Substrate: coform

TABLE 24

Antimicrobial Efficacy Testing results for Exemplary Composition No. 5 on a coform substrate.

| Organism | Initial | Day 7 | Day 14 | Day 28 |
|---|---|---|---|---|
| | | CFU/gram or mL | | |
| S. aureus | 9.5E+05 | <1.0E+01 | <1.0E+01 | <1.0E+01 |
| E. coli | 1.5E+06 | <1.0E+01 | <1.0E+01 | <1.0E+01 |
| P. aeruginosa | 8.9E+05 | >2.5E+04 | <1.0E+01 | <1.0E+01 |
| C. albicans | 8.4E+05 | 3.2E+02 | 1.5E+03 | <1.0E+01 |
| A. brasiliensis | 1.1E+06 | 5.0E+02 | <1.0E+02 | <1.0E+02 |
| B. cepacia | 1.2E+06 | 4.5E+02 | <1.0E+01 | <1.0E+01 |

Antimicrobial Efficacy Testing was also conducted using compositions including the antimicrobial agent of sodium benzoate applied to coform. For example, exemplary composition no. 12 including sodium benzoate at a concentration of 3.5 mmol/L (0.05%), and no antimicrobial boosting agent, was applied to coform and tested, with the results being shown below in Table 25. Exemplary composition no. 12 applied to coform demonstrated similar results as to Table 13 above for the composition itself with unsatisfactory antimicrobial performance against organisms of A. brasiliensis and B. cepacia, however, also had unsatisfactory performance against the organisms of S. aureus, E. coli, P. aeruginosa, and C. albicans when applied to a coform substrate.

Exemplary Composition No. 12 on Substrate

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: None
Substrate: coform

TABLE 25

Antimicrobial Efficacy Testing results for Exemplary Composition No. 12 on a coform substrate.

| Organism | Initial | Day 7 | Day 14 | Day 28 |
|---|---|---|---|---|
| | | CFU/gram or mL | | |
| S. aureus | 7.5E+05 | >2.5E+03 | 4.2E+04 | 4.1E+04 |
| E. coli | 8.9E+05 | 9.2E+02 | >2.5E+05 | 5.3E+03 |
| P. aeruginosa | 5.4E+05 | >2.5E+03 | <1.0E+02 | >2.5E+04 |
| C. albicans | 7.5E+05 | >2.5E+03 | >2.5E+05 | 1.0E+04 |
| A. brasiliensis | 1.2E+06 | 9.5E+03 | 2.8E+05 | 2.7E+04 |
| B. cepacia | 7.4E+05 | >2.5E+03 | >2.5E+05 | >2.5E+05 |

Exemplary composition no. 16 including sodium benzoate at a concentration of 3.5 mmol/L (0.05%) and the antimicrobial boosting agent of lauryl hydroxysultaine at a concentration of 5 mmol/L (0.18%) was also applied to coform and tested, with the results being shown in Table 26 below. As exemplary composition no. 16 demonstrated above in Table 17, the antimicrobial boosting agent of lauryl hydroxysultaine provided improved antimicrobial efficacy for the antimicrobial agent of sodium benzoate against organisms of S. aureus, E. coli, P. aeruginosa, C. albicans, A. brasiliensis, and B. cepacia when the composition was applied to a coform substrate.

Exemplary Composition No. 16 on Substrate

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: lauryl hydroxysultaine (Mackam LHS-E)
Antimicrobial boosting agent concentration: 5.0 mmol/L
Antimicrobial boosting agent blend weight %: 0.37%
Antimicrobial boosting agent active weight %: 0.18%
Substrate: coform

TABLE 26

Antimicrobial Efficacy Testing results for Exemplary Composition No. 16 on a coform substrate.

| Organism | Initial | Day 7 | Day 14 | Day 28 |
|---|---|---|---|---|
| | | CFU/gram or mL | | |
| S. aureus | 8.5E+05 | <1.0E+01 | <1.0E+01 | <1.0E+01 |
| E. coli | 1.5E+06 | <1.0E+01 | <1.0E+01 | <1.0E+01 |
| P. aeruginosa | 9.3E+05 | <1.0E+01 | <1.0E+01 | <1.0E+01 |
| C. albicans | 9.4E+05 | 1.8E+02 | <1.0E+01 | <1.0E+01 |
| A. brasiliensis | 1.4E+06 | 2.00E+02 | <1.0E+02 | <1.0E+02 |
| B. cepacia | 1.1E+06 | <1.0E+01 | <1.0E+01 | <1.0E+01 |

Similar to testing additional surfactants for capability for potential antimicrobial boosting agents described above, exemplary composition 18 including the antimicrobial agent of sodium benzoate and the antimicrobial boosting agent of sodium methyl cocoyl taurate was also applied to a substrate of coform and tested. Surprisingly, while the sodium methyl cocoyl taurate provided improved antimicrobial characteristics for the sodium benzoate in composition form as noted in Table 19 above, the sodium methyl cocoyl taurate did not provide as positive of antimicrobial benefits when used on a substrate of coform, as noted in Table 27 below. In particular, exemplary composition no. 18 did not provide a satisfactory antimicrobial effect for the organisms of A. brasiliensis or B. cepacia when the composition was used on a substrate as it did in composition form (comparing Table 19 and Table 27).

Exemplary Composition No. 18 on Substrate

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: sodium methyl cocoyl taurate (Hostapon CT Paste)
Antimicrobial boosting agent concentration: 8.9 mmol/L
Antimicrobial boosting agent blend weight %: 1.00%
Antimicrobial boosting agent active weight %: 0.30%
Substrate: coform

TABLE 27

Antimicrobial Efficacy Testing results for Exemplary
Composition No. 18 on a coform substrate.

| Organism | Initial | Day 7 | Day 14 | Day 28 |
|---|---|---|---|---|
| | | CFU/gram or mL | | |
| S. aureus | 9.5E+05 | <1.0E+01 | <1.0E+01 | <1.0E+01 |
| E. coli | 1.5E+06 | 2.05E+02 | 3.0E+01 | <1.0E+01 |
| P. aeruginosa | 8.9E+05 | <1.0E+01 | <1.0E+01 | <1.0E+01 |
| C. albicans | 8.4E+05 | >2.5E+04 | <1.0E+01 | <1.0E+01 |
| A. brasiliensis | 1.1E+06 | 1.95E+04 | 1.0E+04 | 1.3E+04 |
| B. cepacia | 1.2E+06 | <1.0E+01 | >2.5E+04 | >2.5E+05 |

As was completed in Antimicrobial Efficacy Testing in the composition form, sodium benzoate was also tested in a composition by itself in significantly higher concentrations when applied to a coform substrate to determine if its antimicrobial effectiveness could be enhanced without any boosting agent. Exemplary compositions 19 and 20 described above provided sodium benzoate at concentrations of 10.5 mmol/L (0.15%) and 17.5 mmol/L (0.25%), respectively, and were applied to a coform substrate. As shown in Tables 28 and 29, increasing the concentration of the antimicrobial agent of sodium benzoate in comparison to the 3.5 mmol/L (0.05%) as was used in composition 12 when applied to a coform substrate (Table 25) did provide for an increase in antimicrobial effectiveness against S. aureus, E. coli, P. aeruginosa, C. albicans, and B. cepacia in both compositions used on the coform substrate (see Tables 28 and 29). As shown in Table 28, raising the concentration of the antimicrobial agent sodium benzoate to only 10.5 mmol/L (0.15%) did not display any increase in the antimicrobial effectiveness against A. brasiliensis, whereas the increase to 17.5 mmol/L (0.25%) of sodium benzoate did provide an adequate increase in antimicrobial effectiveness against A. brasiliensis (as shown in Table 29). However, even at the concentration of 17.5 mmol/L (0.25%) of the antimicrobial agent sodium benzoate, efficacy against B. cepacia was still inferior to the combination of 3.5 mmol/L (0.05%) of the antimicrobial agent sodium benzoate in combination with 5.0 mmol/L (0.18%) of the antimicrobial boosting agent lauryl hydroxysultaine (see Tables 26 and 29). This demonstrates that efficacy equal to or better than that of much higher levels of antimicrobial agents can be achieved by combining the antimicrobial agent with the antimicrobial boosting agent of lauryl hydroxysultaine.

Exemplary Composition No. 19 on Substrate

Antimicrobial agent: sodium benzoate
Antimicrobial agent concentration: 10.5 mmol/L
Antimicrobial agent blend weight %: 0.15%
Antimicrobial agent active weight %: 0.15%
Antimicrobial boosting agent: None
Substrate: coform

TABLE 28

Antimicrobial Efficacy Testing results for Exemplary
Composition No. 19 on a coform substrate.

| Organism | Initial | Day 7 | Day 14 | Day 28 |
|---|---|---|---|---|
| | | CFU/gram or mL | | |
| S. aureus | 8.5E+05 | <1.0E+01 | <1.0E+01 | <1.0E+01 |
| E. coli | 1.5E+06 | <1.0E+01 | <1.0E+01 | <1.0E+01 |
| P. aeruginosa | 9.3E+05 | <1.0E+01 | <1.0E+01 | <1.0E+01 |
| C. albicans | 9.4E+05 | >2.5E+04 | <1.0E+01 | 3.5E+01 |
| A. brasiliensis | 1.4E+06 | 2.90E+04 | 6.5E+04 | 1.2E+05 |
| B. cepacia | 1.1E+06 | <1.0E+01 | <1.0E+01 | <1.0E+01 |

Exemplary Composition No. 20 on Substrate

Antimicrobial agent: sodium benzoate
Antimicrobial agent concentration: 17.5 mmol/L
Antimicrobial agent blend weight %: 0.25%
Antimicrobial agent active weight %: 0.25%
Antimicrobial boosting agent: None
Substrate: coform

TABLE 29

Antimicrobial Efficacy Testing results for Exemplary
Composition No. 20 on a coform substrate.

| Organism | Initial | Day 7 | Day 14 | Day 28 |
|---|---|---|---|---|
| | | CFU/gram or mL | | |
| S. aureus | 8.5E+05 | <1.0E+01 | <1.0E+01 | <1.0E+01 |
| E. coli | 1.5E+06 | <1.0E+01 | <1.0E+01 | <1.0E+01 |
| P. aeruginosa | 9.3E+05 | <1.0E+01 | <1.0E+01 | <1.0E+01 |
| C. albicans | 9.4E+05 | <1.0E+01 | <1.0E+01 | <1.0E+01 |
| A. brasiliensis | 1.4E+06 | <1.0E+02 | <1.0E+02 | <1.0E+02 |
| B. cepacia | 1.1E+06 | 1.1E+03 | <1.0E+01 | <1.0E+01 |

Antimicrobial Efficacy Testing was also completed on an airlaid substrate for compositions including two different antimicrobial agents, as well as compositions including those antimicrobial agents along with the antimicrobial boosting agent of lauryl hydroxysultaine. The airlaid substrate used in testing was a composite airlaid/uncreped, through-air dried tissue substrate. The testing of exemplary compositions on airlaid substrates was completed by applying the exemplary compositions at a rate of 2.3 grams of formulation per gram of dry basesheet to a substrate of airlaid with a basis weight of 87 g/m$^2$.

Exemplary composition no. 4 including 10 mmol/L (0.14%) of hydroxyacetophenone was applied to an airlaid substrate as described above and tested, the results of which are shown in Table 30. As documented in Table 30, the antimicrobial agent of hydroxyacetophenone did not provide satisfactory antimicrobial effectiveness against A. brasiliensis when on an airlaid substrate.

Exemplary Composition No. 4 on Substrate

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: None
Substrate: airlaid

TABLE 30

Antimicrobial Efficacy Testing results for Exemplary
Composition No. 4 on an airlaid substrate.

| Organism | Initial | Day 7 | Day 14 | Day 28 |
|---|---|---|---|---|
| | | CFU/gram or mL | | |
| S. aureus | 7.8E+05 | <1.0E+01 | <1.0E+01 | <1.0E+01 |
| E. coli | 8.1E+05 | 1.2E+02 | <1.0E+01 | <1.0E+01 |
| P. aeruginosa | 6.9E+05 | <1.0E+01 | <1.0E+01 | <1.0E+01 |
| C. albicans | 9.2E+05 | <1.0E+01 | <1.0E+01 | 8.0E+01 |
| A. brasiliensis | 7.5E+05 | 1.8E+03 | 1.9E+04 | 2.9E+05 |
| B. cepacia | 5.7E+05 | <1.0E+01 | <1.0E+01 | <1.0E+01 |

Exemplary composition no. 5 that included the antimicrobial agent of hydroxyacetophenone with the antimicrobial boosting agent of lauryl hydroxysultaine at a concentration of 5 mmol/L (0.18%) was also tested on an airlaid substrate. As shown from the results in Table 31, the antimicrobial boosting agent of lauryl hydroxysultaine used along with the antimicrobial agent of hydroxyacetophenone when tested on an airlaid substrate provided an increase in antimicrobial effectiveness against E. coli, C. albicans and A. brasiliensis compared to exemplary composition no. 4 that only included the antimicrobial agent of hydroxyacetophenone and that was applied to an airlaid substrate (see Table 30). This provides a similarity to the trend noted above regarding synergistic results between the antimicrobial agent of hydroxyacetophenone and the antimicrobial boosting agent of lauryl hydroxysultaine.

Exemplary Composition No. 5 on Substrate

Antimicrobial agent: hydroxyacetophenone (Symsave H)
Antimicrobial agent concentration: 10 mmol/L
Antimicrobial agent blend weight %: 0.14%
Antimicrobial agent active weight %: 0.14%
Antimicrobial boosting agent: lauryl hydroxysultaine (Mackam LHS-E)
Antimicrobial boosting agent concentration: 5 mmol/L
Antimicrobial boosting agent blend weight %: 0.37%
Antimicrobial boosting agent active weight %: 0.18%
Substrate: airlaid

TABLE 31

Antimicrobial Efficacy Testing results for Exemplary
Composition No. 5 on an airlaid substrate.

| Organism | Initial | Day 7 | Day 14 | Day 28 |
|---|---|---|---|---|
| | | CFU/gram or mL | | |
| S. aureus | 7.8E+05 | <1.0E+01 | <1.0E+01 | <1.0E+01 |
| E. coli | 8.1E+05 | <1.0E+01 | <1.0E+01 | <1.0E+01 |
| P. aeruginosa | 6.9E+05 | <1.0E+01 | <1.0E+01 | <1.0E+01 |
| C. albicans | 9.2E+05 | <1.0E+01 | <1.0E+01 | <1.0E+01 |
| A. brasiliensis | 7.5E+05 | 1.0E+04 | 5.0E+03 | 2.5E+04 |
| B. cepacia | 5.7E+05 | <1.0E+01 | <1.0E+01 | <1.0E+01 |

Exemplary composition no. 12 that included the antimicrobial agent of sodium benzoate at a concentration of 3.5 mmol/L (0.050%) was also tested when applied to an airlaid substrate. As shown in Table 32 below, the composition did not provide a satisfactory antimicrobial efficacy against C. albicans, A brasiliensis, or B. cepacia, similar to the testing results when the composition was tested on no substrate and that are documented in Table 13.

Exemplary Composition No. 12 on Substrate

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: None
Composition pH target: 4.1
Substrate: airlaid

TABLE 32

Antimicrobial Efficacy Testing results for Exemplary
Composition No. 12 on an airlaid substrate.

| Organism | Initial | Day 7 | Day 14 | Day 28 |
|---|---|---|---|---|
| | | CFU/gram or mL | | |
| S. aureus | 7.8E+05 | <1.0E+01 | <1.0E+01 | <1.0E+01 |
| E. coli | 8.1E+05 | 2.0E+01 | <1.0E+01 | <1.0E+01 |
| P. aeruginosa | 6.9E+05 | <1.0E+01 | <1.0E+01 | <1.0E+01 |
| C. albicans | 9.2E+05 | <1.0E+01 | 1.6E+03 | 4.2E+03 |
| A. brasiliensis | 7.5E+05 | 6.5E+03 | 1.4E+05 | 4.6E+05 |
| B. cepacia | 5.7E+05 | 6.7E+02 | >2.5E+04 | >2.5E+05 |

Exemplary composition no. 16 that included the antimicrobial agent of sodium benzoate at a concentration of 3.5 mmol/L (0.05%) along with a 5 mmol/L (0.18%) of lauryl hydroxysultaine was also tested on an airlaid substrate. As Table 33 shows, the composition including the antimicrobial agent of sodium benzoate and the antimicrobial boosting agent of lauryl hydroxysultaine applied to an airlaid substrate provided an increase in antimicrobial effectiveness against C. albicans, A brasiliensis, and B. cepacia compared to exemplary composition no. 12 that only included the antimicrobial agent of sodium benzoate and that was applied to an airlaid substrate (see Table 32). This provides a similarity to the trend noted above regarding synergistic results between the antimicrobial agent of sodium benzoate and the antimicrobial boosting agent of lauryl hydroxysultaine.

Exemplary Composition No. 16 on Substrate

Antimicrobial agent: sodium benzoate
Antimicrobial agent concentration: 3.5 mmol/L
Antimicrobial agent blend weight %: 0.05%
Antimicrobial agent active weight %: 0.05%
Antimicrobial boosting agent: lauryl hydroxysultaine (Mackam LHS-E)
Antimicrobial boosting agent concentration: 5.0 mmol/L
Antimicrobial boosting agent blend weight %: 0.37%
Antimicrobial boosting agent active weight %: 0.18%
Composition pH target: 4.1
Substrate: airlaid

TABLE 33

Antimicrobial Efficacy Testing results for Exemplary
Composition No. 16 on an airlaid substrate.

| Organism | Initial | Day 7 | Day 14 | Day 28 |
|---|---|---|---|---|
| | | CFU/gram or mL | | |
| S. aureus | 7.8E+05 | <1.0E+01 | <1.0E+01 | <1.0E+01 |
| E. coli | 8.1E+05 | <1.0E+01 | <1.0E+01 | <1.0E+01 |
| P. aeruginosa | 6.9E+05 | <1.0E+01 | <1.0E+01 | <1.0E+01 |
| C. albicans | 9.2E+05 | <1.0E+01 | <1.0E+01 | <1.0E+01 |
| A. brasiliensis | 7.5E+05 | 3.0E+03 | 1.8E+03 | 5.0E+04 |
| B. cepacia | 5.7E+05 | <1.0E+01 | <1.0E+01 | <1.0E+01 |

From the testing described herein, it was discovered that sultaines proved successful at providing an antimicrobial boosting effect with antimicrobial agents, and in some cases, providing synergistic results. Preferable sultaines that can serve as an antimicrobial boosting agent can include, but are not limited to, lauryl hydroxysultaine, decyl sultaine, lauryl sultaine, lauramidopropyl hydroxysultaine, myristyl sultaine, benzyl sultaine, capryl sultaine, and cocamidopropyl hydroxysultaine.

In some embodiments, sultaines serving as an antimicrobial boosting agent can be in the form shown below.

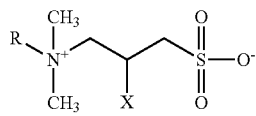

In this structure, R can be a carbon chain having a length of 10 to 16 carbons, X can be a hydrogen or a hydroxide group. Even more preferable sultaines as antimicrobial boosting agents included lauryl hydroxysultaine, decyl sultaine, and lauryl sultaine.

In some embodiments, the antimicrobial boosting agent can provide from about 0.001% to about 1.00% (by total weight of the composition), in some embodiments between about 0.01 to about 0.90% (by total weight of the composition), and in some embodiments, between about 0.01% to about 0.75% (by total weight of the composition). As used herein, the amount the antimicrobial boosting agent provides in a composition is the active weight of the antimicrobial boosting agent by total weight of the composition.

Carriers

The antimicrobial compositions of the present disclosure may be formulated with one or more conventional and compatible carrier materials. The antimicrobial composition may take a variety of forms including, without limitation, aqueous solutions, gels, balms, lotions, suspensions, creams, milks, salves, ointments, sprays, emulsions, oils, resins, foams, solid sticks, aerosols, and the like. Liquid carrier materials suitable for use in the instant disclosure include those well-known for use in the cosmetic, pharmaceutical, and medical arts as a basis for ointments, lotions, creams, salves, aerosols, gels, suspensions, sprays, foams, washes, and the like, and may be used in their established levels. The carrier can comprise from about 0.01% to about 99.98% (by total weight of the composition), depending on the carrier used. In preferred embodiments, the carrier can comprise greater than 90% of the composition (by total weight of the composition). In some preferred embodiments, the carrier can comprise between about 92%-99.98% of the composition (by total weight of the composition).

Preferable carrier materials include polar solvent materials, such as water. Other potential carriers include emollients, humectants, polyols, surfactants, esters, perfluorocarbons, silicones, and other pharmaceutically acceptable carrier materials. In one embodiment, the carrier is volatile, allowing for immediate deposition of the antimicrobial ingredient to the desired surface while improving overall usage experience of the product by reducing drying time. Non-limiting examples of these volatile carriers include 5 cst Dimethicone, Cyclomethicone, Methyl Perfluoroisobutyl Ether, Methyl Perfluorobutyl Ether, Ethyl Perfluoroisobutyl Ether and Ethyl Perfluorobutyl Ether. Unlike conventional volatile carriers such as ethanol or isopropyl alcohol, these carriers have no antimicrobial effect.

In one embodiment, the antimicrobial compositions can optionally include one or more emollients, which typically act to soften, soothe, and otherwise lubricate and/or moisturize the skin. Suitable emollients that can be incorporated into the compositions include oils such as alkyl dimethicones, alkyl methicones, alkyldimethicone copolyols, phenyl silicones, alkyl trimethylsilanes, dimethicone, dimethicone crosspolymers, cyclomethicone, lanolin and its derivatives, fatty esters, fatty acids, glycerol esters and derivatives, propylene glycol esters and derivatives, alkoxylated carboxylic acids, alkoxylated alcohols, fatty alcohols, and combinations thereof.

Some embodiments of the antimicrobial compositions may include one or more emollients in an amount of from about 0.01% (by total weight of the composition) to about 20% (by total weight of the composition), or from about 0.05% (by total weight of the composition) to about 10% (by total weight of the composition), or from about 0.10% (by total weight of the composition) to about 5% (by total weight of the composition).

In some embodiments, the antimicrobial compositions include one or more esters. The esters may be selected from cetyl palmitate, stearyl palmitate, cetyl stearate, isopropyl laurate, isopropyl myristate, isopropyl palmitate, and combinations thereof. The fatty alcohols include octyldodecanol, lauryl, myristyl, cetyl, stearyl, behenyl alcohol, and combinations thereof. The fatty acids can include, but are not limited to, capric acid, undecylenic acid, lauric acid, Myristic acid, palmitic acid, stearic acid, oleic acid, linoleic acid, arachidic acid, and behenic acid. Ethers such as eucalyptol, ceteraryl glucoside, dimethyl isosorbic polyglyceryl-3 cetyl ether, polyglyceryl-3 decyltetradecanol, propylene glycol myristyl ether, and combinations thereof can also suitably be used as emollients. Other suitable ester compounds for use in the antimicrobial compositions or the present disclosure are listed in the *International Cosmetic Ingredient Dictionary and Handbook,* 11th Edition, CTFA, (January, 2006) ISBN-10: 1882621360, ISBN-13: 978-1882621361, and in the 2007 *Cosmetic Bench Reference*, Allured Pub. Corporation (Jul. 15, 2007) ISBN-10: 1932633278, ISBN-13: 978-1932633276, both of which are incorporated by reference herein to the extent they are consistent herewith.

Humectants that are suitable as carriers in the antimicrobial compositions of the present disclosure include, for example, glycerin, glycerin derivatives, hyaluronic acid, hyaluronic acid derivatives, betaine, betaine derivatives, amino acids, amino acid derivatives, glycosaminoglycans, glycols, polyols, sugars, sugar alcohols, hydrogenated starch hydrolysates, hydroxy acids, hydroxy acid derivatives, salts of PCA and the like, and combinations thereof. Specific examples of suitable humectants include honey, sorbitol, hyaluronic acid, sodium hyaluronate, betaine, lactic acid, citric acid, sodium citrate, glycolic acid, sodium glycolate sodium lactate, urea, propylene glycol, butylene glycol, pentylene glycol, ethoxydiglycol, methyl gluceth-10, methyl gluceth-20, polyethylene glycols (as listed in the *International Cosmetic Ingredient Dictionary and Handbook* such as PEG-2 through PEG 10), propanediol, xylitol, maltitol, or combinations thereof.

The antimicrobial compositions of the disclosure may include one or more humectants in an amount of about 0.01% (by total weight of the composition) to about 20% (by total weight of the composition), or about 0.05% (by total weight of the composition) to about 10% by total weight of the composition), or about 0.1% (by total weight of the composition) to about 5.0% (by total weight of the composition).

The antimicrobial compositions may include water. For instance, where the antimicrobial composition is a wetting composition, such as described below for use with a wet wipe, the composition will typically include water. The antimicrobial compositions can suitably comprise water in an amount of from about 0.01% (by total weight of the composition) to about 99.98% (by total weight of the composition), or from about 1.00% (by total weight of the composition) to about 99.98% (by total weight of the composition), or from about 50.00% (by total weight of the composition) to about 99.98% (by total weight of the composition), or from about 75.00% (by total weight of the composition) to about 99.98% (by total weight of the composition). In some embodiments, water can comprise an amount from about 50.00% (by total weight of the composition) to about 70.00% (by total weight of the composition). In some embodiments, water can comprise an amount greater than 90.00% (by total weight of the composition) to about 99.98%.

In an embodiment where the antimicrobial composition serves as a wash (e.g. shampoo; surface cleaner; or hand, face, or body wash), the antimicrobial composition will likely include one or more surfactants. In an embodiment where the antimicrobial composition is included in a wipe, the antimicrobial composition may also likely include one or more surfactants. These may be selected from anionic, cationic, nonionic, zwitterionic, and amphoteric surfactants. Amounts of surfactants may range from 0.01 to 30%, or from 10 to 30%, or from 0.05 to 20%, or from 0.10 to 15% by total weight of the composition. In some embodiments, such as when the wetting composition is used with a wipe, the surfactant can comprise less than 5% by total weight of the wetting composition.

Suitable anionic surfactants include, but are not limited to, $C_8$ to $C_{22}$ alkane sulfates, ether sulfates and sulfonates. Among the suitable sulfonates are primary $C_8$ to $C_{22}$ alkane sulfonate, primary $C_8$ to $C_{22}$ alkane disulfonate, $C_8$ to $C_{22}$ alkene sulfonate, $C_8$ to $C_{22}$ hydroxyalkane sulfonate or alkyl glyceryl ether sulfonate. Specific examples of anionic surfactants include ammonium lauryl sulfate, ammonium laureth sulfate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium laureth sulfate, sodium lauryl sarcosinate, sodium lauroyl sarcosinate, potassium lauryl sulfate, sodium trideceth sulfate, sodium methyl lauroyl taurate, sodium lauroyl isethionate, sodium laureth sulfosuccinate, sodium lauroyl sulfosuccinate, sodium tridecyl benzene sulfonate, sodium dodecyl benzene sulfonate, sodium lauryl amphoacetate and mixtures thereof. Other anionic surfactants include the $C_8$ to $C_{22}$ acyl glycinate salts. Suitable glycinate salts include sodium cocoylglycinate, potassium cocoylglycinate, sodium lauroylglycinate, potassium lauroylglycinate, sodium myristoylglycinate, potassium myristoylglycinate, sodium palmitoylglycinate, potassium palmitoylglycinate, sodium stearoylglycinate, potassium stearoylglycinate, ammonium cocoylglycinate and mixtures thereof. Cationic counter-ions to form the salt of the glycinate may be selected from sodium, potassium, ammonium, alkanolammonium and mixtures of these cations.

Suitable cationic surfactants include, but are not limited to alkyl dimethylamines, alkyl amidopropylamines, alkyl imidazoline derivatives, quaternized amine ethoxylates, and quaternary ammonium compounds.

Suitable nonionic surfactants include, but are not limited to, alcohols, acids, amides or alkyl phenols reacted with alkylene oxides, especially ethylene oxide either alone or with propylene oxide. Specific nonionics are $C_6$ to $C_{22}$ alkyl phenols-ethylene oxide condensates, the condensation products of $C_8$ to $C_{13}$ aliphatic primary or secondary linear or branched alcohols with ethylene oxide, and products made by condensation of ethylene oxide with the reaction products of propylene oxide and ethylenediamine. Other nonionics include long chain tertiary amine oxides, long chain tertiary phosphine oxides and dialkyl sulphoxides, alkyl polysaccharides, amine oxides, block copolymers, castor oil ethoxylates, ceto-oleyl alcohol ethoxylates, ceto-stearyl alcohol ethoxylates, decyl alcohol ethoxylates, dinonyl phenol ethoxylates, dodecyl phenol ethoxylates, end-capped ethoxylates, ether amine derivatives, ethoxylated alkanolamides, ethylene glycol esters, fatty acid alkanolamides, fatty alcohol alkoxylates, lauryl alcohol ethoxylates, monobranched alcohol ethoxylates, natural alcohol ethoxylates, nonyl phenol ethoxylates, octyl phenol ethoxylates, oleyl amine ethoxylates, random copolymer alkoxylates, sorbitan ester ethoxylates, stearic acid ethoxylates, stearyl amine ethoxylates, synthetic alcohol ethoxylates, tall oil fatty acid ethoxylates, tallow amine ethoxylates and tridecanol ethoxylates.

Suitable zwitterionic surfactants include, for example, alkyl amine oxides, alkyl hydroxysultaines, silicone amine oxides, and combinations thereof. Specific examples of suitable zwitterionic surfactants include, for example, 4-[N,N-di(2-hydroxyethyl)-N-octadecylammonio]-butane-1-carboxylate, S—[S-3-hydroxypropyl-S-hexadecylsulfonio]-3-hydroxypentane-1-sulfate, 3-[P,P-diethyl-P-3,6,9-trioxatetradexopcylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio]-propane-1-phosphate, 3-[P,P-dimethyl-P-dodecylphosphonio]-propane-1-phosphonate, 5-[N,N-di(3-hydroxypropyl)-N-hexadecylammonio]-2-hydroxy-pentane-1-sulfate and combinations thereof.

Suitable amphoteric surfactants include, but are not limited to, derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one substituent contains an anionic group, e.g., carboxy, sulfonate, sulfate, phosphate, or phosphonate. Illustrative amphoterics are coco dimethyl carboxymethyl betaine, cocoamidopropyl betaine, cocobetaine, oleyl betaine, cetyl dimethyl carboxymethyl betaine, lauryl bis-(2-hydroxyethyl) carboxymethyl betaine, stearyl bis-(2-hydroxypropyl) carboxymethyl betaine, oleyl dimethyl gamma-carboxypropyl betaine, lauryl bis-(2-hydroxypropyl)alpha-carboxyethyl betaine, cocoamphoacetates, and combinations thereof. The sulfobetaines may include stearyl dimethyl sulfopropyl betaine, lauryl dimethyl sulfoethyl betaine, lauryl bis-(2-hydroxyethyl) sulfopropyl betaine and combinations thereof.

Rheology Modifier

Optionally, one or more rheology modifiers, such as thickeners, may be added to the antimicrobial compositions. Suitable rheology modifiers are compatible with the antimicrobial agent. As used herein, "compatible" refers to a compound that, when mixed with the antimicrobial agent, does not adversely affect the antimicrobial properties of same.

A thickening system is used in the antimicrobial compositions to adjust the viscosity and stability of the compositions. Specifically, thickening systems prevent the composition from running off of the hands or body during dispensing and use of the composition. When the antimicrobial composition is used with a wipe product, a thicker formulation can be used to prevent the composition from migrating from the wipe substrate.

The thickening system should be compatible with the compounds used in the present disclosure; that is, the thickening system, when used in combination with the antimicrobial compounds, should not precipitate out, form a coacervate, or prevent a user from perceiving the conditioning benefit (or other desired benefit) to be gained from the composition. The thickening system may include a thickener which can provide both the thickening effect desired from the thickening system and a conditioning effect to the user's skin.

Thickeners may include, cellulosics, gums, acrylates, starches and various polymers. Suitable examples include but are not limited to hydroxethyl cellulose, xanthan gum, guar gum, potato starch, and corn starch. In some embodiments, PEG-150 stearate, PEG-150 distearate, PEG-175 diisostearate, polyglyceryl-10 behenate/eicosadioate, disteareth-100 IPDI, polyacrylamidomethylpropane sulfonic acid, butylated PVP, and combinations thereof may be suitable.

While the viscosity of the compositions will typically depend on the thickener used and the other components of the compositions, the thickeners of the compositions suitably provide for a composition having a viscosity in the range of greater than 1 cP to about 30,000 cP or more. In another embodiment, the thickeners provide compositions having a viscosity of from about 100 cP to about 20,000 cP. In yet another embodiment, thickeners provide compositions having a viscosity of from about 200 cP to about 15,000 cP. In embodiments where the compositions are included in a wipe, the viscosity may range from about 1 cP to about 2000 cP. In some embodiments, it is preferable to have a viscosity of the composition be less than 500 cP.

Typically, the antimicrobial compositions of the present disclosure include the thickening system in an amount of no more than about 20% (by total weight of the composition), or from about 0.01% (by total weight of the composition) to about 20% (by total weight of the composition). In another aspect the thickening system is present in the antimicrobial composition in an amount of from about 0.10% (by total weight of the composition) to about 10% (by total weight of the composition), or from about 0.25% (by total weight of the composition) to about 5% (by total weight of the composition), or from about 0.5% (by total weight of the composition) to about 2% (by total weight of the composition).

Emulsifiers

In one embodiment, the antimicrobial compositions may include hydrophobic and hydrophilic ingredients, such as a lotion or cream. Generally, these emulsions have a dispersed phase and a continuous phase, and are generally formed with the addition of a surfactant or a combination of surfactants with varying hydrophilic/lipophilic balances (HLB). Suitable emulsifiers include surfactants having HLB values from 0 to 20, or from 2 to 18. Suitable non-limiting examples include Ceteareth-20, Cetearyl Glucoside, Ceteth-10, Ceteth-2, Ceteth-20, Cocamide MEA, Glyceryl Laurate, Glyceryl Stearate, PEG-100 Stearate, Glyceryl Stearate, Glyceryl Stearate SE, Glycol Distearate, Glycol Stearate, Isosteareth-20, Laureth-23, Laureth-4, Lecithin, Methyl Glucose Sesquistearate, Oleth-10, Oleth-2, Oleth-20, PEG-100 Stearate, PEG-20 Almond Glycerides, PEG-20 Methyl Glucose Sesquistearate, PEG-25 Hydrogenated Castor Oil, PEG-30 Dipolyhydroxystearate, PEG-4 Dilaurate, PEG-40 Sorbitan Peroleate, PEG-60 Almond Glycerides, PEG-7 Olivate, PEG-7 Glyceryl Cocoate, PEG-8 Dioleate, PEG-8 Laurate, PEG-8 Oleate, PEG-80 Sorbitan Laurate, Polysorbate 20, Polysorbate 60, Polysorbate 80, Polysorbate 85, Propylene Glycol Isostearate, Sorbitan Isostearate, Sorbitan Laurate, Sorbitan Monostearate, Sorbitan Oleate, Sorbitan Sesquioleate, Sorbitan Stearate, Sorbitan Trioleate, Stearamide MEA, Steareth-100, Steareth-2, Steareth-20, Steareth-21. The compositions can further include surfactants or combinations of surfactants that create liquid crystalline networks or liposomal networks. Suitable non-limiting examples include OLIVEM 1000 (INCI: Cetearyl Olivate (and) Sorbitan Olivate (available from HallStar Company (Chicago, IL)); ARLACEL LC (INCI: Sorbitan Stearate (and) Sorbityl Laurate, commercially available from Croda (Edison, NJ)); CRYSTALCAST MM (INCI: Beta Sitosterol (and) Sucrose Stearate (and) Sucrose Distearate (and) Cetyl Alcohol (and) Stearyl Alcohol, commercially available from MMP Inc. (South Plainfield, NJ)); UNIOX CRISTAL (INCI: Cetearyl Alcohol (and) Polysorbate 60 (and) Cetearyl Glucoside, commercially available from Chemyunion (Sho Paulo, Brazil)). Other suitable emulsifiers include lecithin, hydrogenated lecithin, lysolecithin, phosphatidylcholine, phospholipids, and combinations thereof.

Adjunct Ingredients

The antimicrobial compositions of the present disclosure may additionally include adjunct ingredients conventionally found in cosmetic, pharmaceutical, medical, household, industrial, or personal care compositions/products in an established fashion and at established levels. For example, the antimicrobial compositions may comprise additional compatible pharmaceutically active and compatible materials for combination therapy, such as antioxidants, antiparasitic agents, antipruritics, antifungals, antiseptic actives, biological actives, astringents, keratolytic actives, local anaesthetics, anti-stinging agents, anti-reddening agents, skin soothing agents, external analgesics, film formers, skin exfoliating agents, sunscreens, and combinations thereof.

Other suitable additives that may be included in the antimicrobial compositions of the present disclosure include compatible colorants, deodorants, emulsifiers, anti-foaming agents (when foam is not desired), lubricants, skin conditioning agents, skin protectants and skin benefit agents (e.g., aloe vera and tocopheryl acetate), solvents (e.g., water soluble glycol and glycol ethers, glycerin, water soluble polyethylene glycols, water soluble polyethylene glycol ethers, water soluble polypropylene glycols, water soluble polypropylene glycol ethers, dimethylisosorbide), solubilizing agents, suspending agents, builders, (e.g., alkali and alkaline earth metal salts of carbonate, bicarbonate, phosphate, hydrogen phosphate, dihydrogen phosphate, sulfate hydrogen sulfate), wetting agents, pH adjusting ingredients (a suitable pH range of the compositions can be from about 3.5 to about 8), chelators, propellants, dyes and/or pigments, and combinations thereof.

Another component that may be suitable for addition to the antimicrobial compositions is a fragrance. Any compatible fragrance may be used. Typically, the fragrance is present in an amount from about 0% (by weight of the composition) to about 5% (by weight of the composition), and more typically from about 0.01% (by weight of the composition) to about 3% (by weight of the composition). In one desirable embodiment, the fragrance will have a clean, fresh and/or neutral scent to create an appealing delivery vehicle for the end consumer.

Organic sunscreens that may be present in the antimicrobial compositions include ethylhexyl methoxycinnamate, avobenzone, octocrylene, benzophenone-4, phenylbenzimidazole sulfonic acid, homosalate, oxybenzone, benzophenone-3, ethylhexyl salicylate, and mixtures thereof.

In some embodiments, the antimicrobial composition is substantially free from a short-chain alcohol. As used herein, "substantially free" will mean there is 0.01% or less of a short-chain alcohol in the composition (by total weight of the composition). As used herein, "short-chain alcohol" will mean an alcohol with a single hydroxyl group and a total number of carbon atoms between one and five, inclusive. Non-limiting examples of short-chain alcohols include methanol, ethanol, propanol, isopropyl alcohol, butanol, t-butanol, 2-butanol, pentanol or combinations thereof.

Delivery Vehicles

The antimicrobial compositions of the present disclosure may be used in combination with a product that can serve as a delivery vehicle for the antimicrobial composition. For example, the antimicrobial composition may be incorporated into or onto a substrate, such as a wipe substrate, an absorbent substrate, a fabric or cloth substrate, a tissue or paper towel substrate, or the like. In one embodiment, the antimicrobial composition may be used in combination with a wipe substrate to form a wet wipe or may be a wetting composition for use in combination with a wipe which may be dispersible. In other embodiments, the antimicrobial composition may be incorporated into wipes such as wet wipes, hand wipes, face wipes, cosmetic wipes, cloths and the like. In yet other embodiments, the antimicrobial compositions described herein can be used in combination with numerous personal care products, such as absorbent articles. Absorbent articles of interest are diapers, training pants, adult incontinence products, feminine hygiene products, and the like; bath or facial tissue; and paper towels. Personal protective equipment articles of interest include but are not limited to masks, gowns, gloves, caps, and the like.

In one embodiment, the wet wipe may comprise a nonwoven material that is wetted with an aqueous solution termed the "wetting composition," which may include or be composed entirely of the antimicrobial compositions disclosed herein. As used herein, the nonwoven material comprises a fibrous material or substrate, where the fibrous material or substrate comprises a sheet that has a structure of individual fibers or filaments randomly arranged in a mat-like fashion. Nonwoven materials may be made from a variety of processes including, but not limited to, airlaid processes, wet-laid processes such as with cellulosic-based tissues or towels, hydroentangling processes, staple fiber carding and bonding, melt blown, and solution spinning.

The fibers forming the fibrous material may be made from a variety of materials including natural fibers, synthetic fibers, and combinations thereof. The choice of fibers may depend upon, for example, the intended end use of the finished substrate and the fiber cost. For instance, suitable fibers may include, but are not limited to, natural fibers such as cotton, linen, jute, hemp, wool, wood pulp, etc. Similarly, suitable fibers may also include: regenerated cellulosic fibers, such as viscose rayon and cuprammonium rayon; modified cellulosic fibers, such as cellulose acetate; or synthetic fibers, such as those derived from polypropylenes, polyethylenes, polyolefins, polyesters, polyamides, polyacrylics, etc. Regenerated cellulose fibers, as briefly discussed above, include rayon in all its varieties as well as other fibers derived from viscose or chemically modified cellulose, including regenerated cellulose and solvent-spun cellulose, such as Lyocell. Among wood pulp fibers, any known papermaking fibers may be used, including softwood and hardwood fibers. Fibers, for example, may be chemically pulped or mechanically pulped, bleached or unbleached, virgin or recycled, high yield or low yield, and the like. Chemically treated natural cellulosic fibers may be used, such as mercerized pulps, chemically stiffened or crosslinked fibers, or sulfonated fibers.

In addition, cellulose produced by microbes and other cellulosic derivatives may be used. As used herein, the term "cellulosic" is meant to include any material having cellulose as a major constituent, and, specifically, comprising at least 50 percent by weight cellulose or a cellulose derivative. Thus, the term includes cotton, typical wood pulps, non-woody cellulosic fibers, cellulose acetate, cellulose triacetate, rayon, thermomechanical wood pulp, chemical wood pulp, debonded chemical wood pulp, milkweed, or bacterial cellulose. Blends of one or more of any of the previously described fibers may also be used, if so desired.

The fibrous material may be formed from a single layer or multiple layers. In the case of multiple layers, the layers are generally positioned in a juxtaposed or surface-to-surface relationship and all or a portion of the layers may be bound to adjacent layers. The fibrous material may also be formed from a plurality of separate fibrous materials wherein each of the separate fibrous materials may be formed from a different type of fiber.

Airlaid nonwoven fabrics are particularly well suited for use as wet wipes. The basis weights for airlaid nonwoven fabrics may range from about 20 to about 200 grams per square meter (gsm) with staple fibers having a denier of about 0.5 to about 10 and a length of about 6 to about 15 millimeters. Wet wipes may generally have a fiber density of about 0.025 g/cc to about 0.2 g/cc. Wet wipes may generally have a basis weight of about 20 gsm to about 150 gsm. More desirably the basis weight may be from about 30 to about 90 gsm. Even more desirably the basis weight may be from about 50 gsm to about 75 gsm.

Processes for producing airlaid non-woven basesheets are described in, for example, published U.S. Pat. App. No. 2006/0008621, herein incorporated by reference to the extent it is consistent herewith.

In some embodiments when the antimicrobial composition is used as a wetting composition with a substrate, the wetting composition can be applied to the substrate at an add-on percentage of from about 30% to about 500%, or from about 125% to about 400%, or from about 150% to about 350%.

Test Methods

Minimum Effective Concentration Test Method

The Minimum Effective Concentration Test Method discussed herein began by adding $B.$ $cepacia$ (ATCC 25416) culture at a final concentration of approximately $5\times10^6$ CFU/mL to the composition to be challenged. The challenged composition was then allowed to incubate at room temperature for 24 hours. After 24 hours, a preservative neutralizing broth was added to the mixture and measurements were subsequently taken to determine the concentration of $B.$ $cepacia$ still remaining after exposure to the test composition.

The Minimum Effective Concentration was determined by completing the process described above on a series of compositions with the same concentration of antimicrobial boosting agent, but with different concentrations of antimicrobial agent. The Minimum Effective Concentration of antimicrobial agent for any given value of antimicrobial boosting agent was defined as the minimum concentration of antimicrobial agent required to reduce the concentration of *B. cepacia* to a level below the detection threshold for the test method, which was approximately 100 CFU/mL. In instances where multiple rounds of Minimum Effective Concentration testing were completed, the value reported is the mean of the Minimum Effective Concentration values generated by each individual series of tests.

Antimicrobial Efficacy Testing

The Antimicrobial Efficacy Testing discussed herein was completed pursuant to the standard antimicrobial effectiveness test from Chapter 51 of the United States Pharmacopeia (USP 51), in which an antimicrobial composition can be tested against at least five microorganisms, including bacteria and fungi. In the Antimicrobial Efficacy Testing conducted herein, the following bacteria were utilized: *Staphylococcus aureus, Escherichia* co/i, *Pseudomonas aeruginosa*, and *Burkholderia cepacia*; and the following fungi were utilized: *Candida albicans*, and *Aspergillus brasiliensis*. While one of ordinary skill in the art could replicate such Antimicrobial Efficacy Testing by completing USP 51 protocol, a brief summary was that each antimicrobial composition sample was tested against each microorganism being held at room temperature over the course of 28 days, with each sample being evaluated at specific intervals at the beginning of the Testing (initial), day 7, day 14, and day 28. The test sample colonies were counted at each interval to determine the number of surviving microorganisms. The log reduction of each microorganism at each interval was reported. The effectiveness of the antimicrobial agent sample was based on the USP 51 passing criteria.

Embodiments

Embodiment 1: A composition comprising: a carrier providing at least 90% of a total weight of the composition; an antimicrobial agent; and an antimicrobial boosting agent comprising a sultaine, the antimicrobial boosting agent providing 1.0% or less of the total weight of the composition; wherein the composition is substantially free from a short-chain alcohol.

Embodiment 2: The composition of embodiment 1, wherein the sultaine comprises:

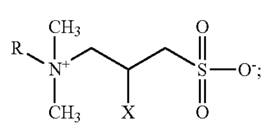

wherein R is a carbon chain having a length of 10 to 16 carbons.

Embodiment 3: The composition of embodiment 2, wherein X is hydrogen or a hydroxide group.

Embodiment 4: The composition of any one of the preceding embodiments, wherein the sultaine comprises lauryl hydroxysultaine, decyl sultaine, myristyl sultaine, or lauryl sultaine.

Embodiment 5: The composition of any one of the preceding embodiments, wherein the antimicrobial agent provides between about 0.01% to about 1.0% of the composition (by total weight of the composition).

Embodiment 6: The composition of any one of the preceding embodiments, wherein the antimicrobial boosting agent provides between about 0.01% to about 0.75% of the composition (by total weight of the composition).

Embodiment 7: The composition of any one of the preceding embodiments, wherein the carrier is water, and wherein water provides between about 92% to about 99.98% of the composition (by total weight of the composition).

Embodiment 8: A method of increasing the antimicrobial effectiveness of an antimicrobial composition, the method comprising: providing an antimicrobial composition comprising: a carrier; and an antimicrobial agent; wherein the composition is substantially free from a short-chain alcohol; selecting an antimicrobial boosting agent comprising a sultaine, the antimicrobial boosting agent being selected to increase the antimicrobial effectiveness of the antimicrobial agent; and adding the antimicrobial boosting agent to the antimicrobial composition to increase the antimicrobial effectiveness of the antimicrobial composition.

Embodiment 9: The method of embodiment 8, wherein the carrier provides at least 90% of a total weight of the composition.

Embodiment 10: The method of embodiment 8 or embodiment 9, wherein the antimicrobial boosting agent provides 1.0% or less of a total weight of the composition.

Embodiment 11: The method of any one of embodiments 8-10, wherein the sultaine comprises:

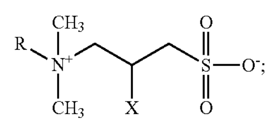

wherein R is a carbon chain having a length of 10 to 16 carbons, and wherein X is hydrogen or a hydroxide group.

Embodiment 12: The method of any one of embodiments 8-11, wherein the sultaine comprises lauryl hydroxysultaine, decyl sultaine, myristyl sultaine, or lauryl sultaine.

Embodiment 13: The method of any one of embodiments 8-12, wherein the antimicrobial agent provides between about 0.01% to about 1.0% of the composition (by total weight of the composition).

Embodiment 14: The method of any one of embodiments 8-13, wherein the antimicrobial boosting agent provides between about 0.01% to about 0.75% of the composition (by total weight of the composition).

Embodiment 15: The method of any one of embodiments 8-14, wherein the carrier is water.

Embodiment 16: The method of embodiment 15, wherein water provides between about 92% to about 99.98% of the composition (by total weight of the composition).

Embodiment 17: A wet wipe comprising: a substrate; and a wetting composition applied to the substrate, the wetting composition comprising: a carrier, the carrier providing at least 90% of a total weight of the wetting composition; an antimicrobial agent; and an antimicrobial boosting agent comprising a sultaine, the antimicrobial boosting agent providing 1.0% or less of the total weight of the wetting composition; wherein the wetting composition is substantially free from a short-chain alcohol.

Embodiment 18: The wet wipe of embodiment 17, wherein the sultaine comprises:

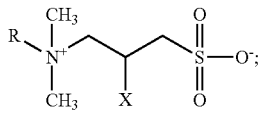

wherein R is a carbon chain having a length of 10 to 16 carbons, and wherein X is hydrogen or a hydroxide group.

Embodiment 19: The wet wipe of embodiment 17 or embodiment 18, wherein the sultaine comprises lauryl hydroxysultaine or myristyl sultaine.

Embodiment 20: The wet wipe of any one of embodiments 17-19, wherein the carrier is water and provides between 92%-99.98% of the composition (by total weight of the composition), and wherein the antimicrobial agent provides between about 0.01% to about 0.75% of the composition (by total weight of the composition).

When introducing elements of the present disclosure, the articles "a", "an", "the" and "said" are intended to mean that there are one or more of the elements. The terms "comprising", "including" and "having" are intended to be inclusive and mean that there may be additional elements other than the listed elements. Many modifications and variations of the present disclosure can be made without departing from the spirit and scope thereof. Therefore, the exemplary embodiments described above should not be used to limit the scope of the disclosure.

What is claimed is:

1. A method of increasing the antimicrobial effectiveness of an antimicrobial composition, the method comprising:
   providing an antimicrobial composition comprising:
      a carrier providing at least 92% of a total weight of the antimicrobial composition;
      an antimicrobial agent comprising at least one of 4'-hydroxyacetophenone and sodium benzoate; and
      an antimicrobial boosting agent, wherein the antimicrobial boosting agent provides between 0.001% to less than 1.0% of a total weight of the antimicrobial composition;
   wherein the antimicrobial composition is substantially free from a short-chain alcohol;
   selecting the antimicrobial boosting agent comprising a sultaine, the antimicrobial boosting agent being selected to increase the antimicrobial effectiveness of the antimicrobial agent, wherein the sultaine comprises at least one of lauryl hydroxysultaine and myristyl sultaine; and
   adding the antimicrobial boosting agent to the antimicrobial composition to increase the antimicrobial effectiveness of the antimicrobial composition such that the antimicrobial composition reduces a population of at least a majority of *Staphylococcus aureus, Escherichia coli, Pseudomonas aeruginosa, Burkholderia cepacian, Candida albicans,* and *Aspergillus brasiliensis* to be less than or equal to 1.0E+02 at Day 7 according to the Antimicrobial Efficacy Test;
   wherein the antimicrobial composition is configured such that the antimicrobial agent comprises 4'-hydroxyacetophenone and the sultaine comprises lauryl hydroxysultaine, or such that the antimicrobial agent comprises sodium benzoate and the sultaine comprises at least one of lauryl hydroxysultaine and myristyl sultaine.

2. The method of claim 1, wherein the carrier provides at least about 95% of a total weight of the antimicrobial composition.

3. The method of claim 1, wherein the antimicrobial agent provides between about 0.01% to less than 1.0% of the antimicrobial composition by total weight of the antimicrobial composition.

4. The method of claim 3, wherein the antimicrobial boosting agent provides between about 0.01% to about 0.75% of the antimicrobial composition by total weight of the antimicrobial composition.

5. The method of claim 1, wherein the carrier is water.

6. The method of claim 5, wherein water provides between about 92% to about 99.98% of the antimicrobial composition by total weight of the antimicrobial composition.

7. The method of claim 1, wherein the antimicrobial composition is configured such that the antimicrobial agent comprises 4'-hydroxyacetophenone and the sultaine comprises lauryl hydroxysultaine.

8. The method of claim 1, wherein the antimicrobial composition is configured such that the antimicrobial agent comprises sodium benzoate and the sultaine comprises at least one of lauryl hydroxysultaine and myristyl sultaine.

* * * * *